US012109131B2

(12) United States Patent
Sanders et al.

(10) Patent No.: US 12,109,131 B2
(45) Date of Patent: Oct. 8, 2024

(54) MOTORIZED ADJUSTABLE SOCKET FOR AMPUTEE PROSTHESIS USERS AND METHODS FOR USE THEREOF

(71) Applicant: University of Washington, Seattle, WA (US)

(72) Inventors: Joan E. Sanders, Seattle, WA (US); Joseph L. Garbini, Seattle, WA (US); Jake McLean, Seattle, WA (US); Jacob Brzostowski, Seattle, WA (US); Christian B. Redd, Seattle, WA (US); John Cagle, Seattle, WA (US); Samuel Bennett, Seattle, WA (US); Horace Wang, Seattle, WA (US); Ethan Weathersby, Seattle, WA (US); Andrew Vamos, Seattle, WA (US)

(73) Assignee: University of Washington, Seattle, WA (US)

( * ) Notice: Subject to any disclaimer, the term of this patent is extended or adjusted under 35 U.S.C. 154(b) by 588 days.

(21) Appl. No.: 16/865,088

(22) Filed: May 1, 2020

(65) Prior Publication Data
US 2020/0345520 A1     Nov. 5, 2020

Related U.S. Application Data

(60) Provisional application No. 62/841,655, filed on May 1, 2019.

(51) Int. Cl.
*A61F 2/80*     (2006.01)
*A61F 2/70*     (2006.01)
(Continued)

(52) U.S. Cl.
CPC ............ *A61F 2/76* (2013.01); *A61F 2/70* (2013.01); *A61F 2/80* (2013.01);
(Continued)

(58) Field of Classification Search
None
See application file for complete search history.

(56) References Cited

U.S. PATENT DOCUMENTS

| 4,695,509 A | 9/1987 | Cordova et al. |
| 5,323,650 A | 6/1994 | Fullen et al. |

(Continued)

OTHER PUBLICATIONS

Newton RL, Morgan D, Schreiber MH. Radiological evaluation of prosthetic fit in below-the-knee amputees. SkeletalRadiol. 1988;17(14):276-80. [PMID: 3212490].

(Continued)

*Primary Examiner* — David H Willse
(74) *Attorney, Agent, or Firm* — McDonnell Boehnen Hulbert & Berghoff LLP

(57) ABSTRACT

The disclosure provides example apparatus and methods for automatically adjusting a socket size of a prosthesis. The apparatus includes (a) the prosthesis having a socket configured to receive a limb, (b) a first opening in a socket wall, (c) a first panel aligned with the first opening, (d) a first actuator coupled to the first panel and to the prosthesis, the first actuator is configured to advance and retract the first panel, (e) a first sensor coupled to the socket wall and configured to obtain limb-to-socket gap data, and (f) a processor coupled to the first actuator and the first sensor, wherein the processor is configured (i) to receive the limb-to-socket gap data, (ii) to determine a socket-size adjustment based on the limb-to-socket gap data and a predetermined socket-fit value, (iii) to generate and (iv) to send a command with the socket-size adjustment to the first actuator.

18 Claims, 14 Drawing Sheets

(51) Int. Cl.
*A61F 2/76* (2006.01)
*A61F 2/78* (2006.01)
*A61F 2/50* (2006.01)
*A61F 2/68* (2006.01)

(52) U.S. Cl.
CPC .......... *A61F 2002/5027* (2013.01); *A61F 2002/6863* (2013.01); *A61F 2002/701* (2013.01); *A61F 2002/704* (2013.01); *A61F 2002/762* (2013.01); *A61F 2002/7818* (2013.01); *A61F 2002/7875* (2013.01)

(56) References Cited

U.S. PATENT DOCUMENTS

| | | | |
|---|---|---|---|
| 5,408,873 | A | 4/1995 | Schmidt et al. |
| 5,507,836 | A | 4/1996 | Pohlig |
| 5,728,165 | A | 3/1998 | Brown, Sr. |
| 5,840,047 | A | 11/1998 | Stedham |
| 6,671,531 | B2 | 12/2003 | Al-Ali et al. |
| 7,377,944 | B2 | 5/2008 | Janusson et al. |
| 8,142,369 | B2 | 3/2012 | Sanders et al. |
| 8,443,501 | B2 | 5/2013 | Mahon |
| 8,480,759 | B2 * | 7/2013 | Pacanowsky ........ A61F 2/80 623/36 |
| 8,869,626 | B2 | 10/2014 | Clausen et al. |
| 8,978,224 | B2 | 3/2015 | Hurley et al. |
| 9,044,159 | B2 | 6/2015 | Sanders et al. |
| 2004/0181290 | A1 | 9/2004 | Caspers |
| 2007/0191965 | A1 * | 8/2007 | Colvin ........ A61F 2/80 623/24 |
| 2010/0023149 | A1 | 1/2010 | Sanders et al. |
| 2012/0041567 | A1 | 2/2012 | Cornell |
| 2013/0123940 | A1 | 5/2013 | Hurley et al. |
| 2014/0149082 | A1 | 5/2014 | Sanders et al. |
| 2017/0143520 | A1 | 5/2017 | Hurley et al. |
| 2017/0156896 | A1 | 6/2017 | Alley |
| 2018/0020973 | A1 | 1/2018 | Hurley et al. |
| 2021/0113356 | A1 * | 4/2021 | Laszczak ........ A61F 2/80 |

OTHER PUBLICATIONS

Grevsten S, Erikson U. A roentgenological study of the stump-socket contact and skeletal displacement in the PTB-Suction Prosthesis. Ups J Med Sci. 1975;80(1):49-57.[PMID: 1145905].

Lilja M, Johansson T, Oberg T. Movement of the tibial end in a PTB prosthesis socket: A sagittal X-ray study of the PTB prosthesis. Prosthet Orthot Int. 1993;17(1):21-26.[PMID: 8337097].

Narita H, Yokogushi K, Shii S, Kakizawa M, Nosaka T. Suspension effect and dynamic evaluation of the total surface bearing (TSB) trans-tibial prosthesis: A comparison with the pateallar tendon bearing (PTB) trans-tibial prosthesis. Pros-thet Orthot Int. 1997;21(3):175-78. [PMID: 9453088].

Kahle JT. A case study using fluoroscope to determine the vital elements of transfemoral interface design. J ProsthetOrthot. 2002;14(3):121-26.

Söderberg B et al. Roentgen stereophotogrammetric analysis of motion between the bone and the socket in a transtibial amputation prosthesis: A case study. J Prosthet Orthot. 2003;15(3):95-99.

Murray KD, Convery P. The calibration of ultrasound transducers used to monitor motion of the residual femur within a trans-femoral socket during gait. Prosthet OrthotInt. 2000;24(1):55-62. [PMID: 10855439].

Convery P, Murray KD. Ultrasound study of the motion of the residual femur within a trans-femoral socket during gait. Prosthet Orthot Int. 2000;24(3):226-32. [PMID: 11195358].

Berme N, Lawes P, Solomonidis S, Paul JP. A shorter pylon transducer for measurement of prosthetic forces and moments during amputee gait. Eng Med. 1976;4(4):6-8.

Sanders JE, Zachariah SG, Jacobsen AK, Fergason JR. Changes in interface pressures and shear stresses over time on trans-tibial amputee subjects ambulating with prosthetic limbs: Comparison of diurnal and six-month differences. J Biomech. 2005;38(8):1566-73. [PMID: 15958212].

Zachariah SG, Saxena R, Fergason JR, Sanders JE. Shape and volume change in the transtibial residuum over the short term: Preliminary investigation of six subjects. J Rehabil ResDev. 2004;41(5):683-94. [PMID: 15558398].

Sanders JE, Daly CH, Burgess EM. Clinical measurement of normal and shear stresses on a trans-tibial stump: Characteristics of waveform shapes during walking. ProsthetOrthot Int. 1993;17(1):38-48. [PMID: 8337099].

Mitchell SB, Sanders JE. An accurate inexpensive system for the assessment of walking speed. J Prosthet Orthot.2000;12(4):117-19.

Polliack AA, Sieh RC, Craig DD, Landsberger S, McNeil DR, Ayyappa E. Scientific validation of two commercial pressure sensor system for prosthetic socket fit. Prosthetics and Orthotics Intl 2000 vol. 24 pp. 63-73.

Force Sensing Prosthetic Leg Liner Measures Pressures to Better Fit New Devices for Amputees. Eds., medGadget Apr. 16, 2014.

Dear-Southampton, Sophie. 'Smart' liner detects how leg prosthetics fit. Futurity, Apr. 17, 2014.

Al-Fakih EA, Osman NAA, Adikan FRM. Techniquest for interface Stress Measurements within Prosthetic Sockets of Transtibial Amputees: A Review of the Past 50 Years of Research. Sensors 2016; 16; 1119.

Grevsten S and Eriksson U. Stump-socket contact and skeletal displacement in a suction patellar-tendon bearing prosthesis. J Bone Joint Surg 1974;56:1692-1696.

Grevsten S. Ideas on the suspension of the below-knee prosthesis. Prosthet Orthot Int 1978; 2: 3-7.

Commean PK, Smith KE and Vannier MW. Lower extremity residual limb slippage within the prosthesis. Arch Phys Med Rehabil 1997; 78: 476-485.

Fernie G and Holliday P. Volume fluctuations in the residual limbs of lower limb amputees. Arch Phys Med Rehabil 1982; 63: 162-165.

Hafner BJ and Sanders JE. Considerations for development of sensing and monitoring tools to facilitate treatment and care of persons with lower limb loss: A review. J Rehabil Res Dev 2014; 51(1): 1-14.

Sanders JE, Karchin A, Fergason JR, Sorenson, Ea. A noncontact sensor for measurement of distal residual-limb position during walking. J Rehabil Res Dev 2006; 43(4): 509-516.

Gerschutz MJ, Hayne ML, Colvin JM, Denune JA. Dynamic effectiveness evaluation of elevated vacuum suspension. J Prosthet Orthot 2015; 27: 161-165.

Board WJ, Street GM and Caspers C. A comparison of trans-tibial amputee suction and vacuum socket conditions. Prosthet Orthot Int 2001; 25(3): 202-209.

Swanson EC, McLean JB, Allyn KJ, Redd CB, Sanders JE. Instrumented socket inserts for sensing interaction at the limb-socket interface. Med EngPhys 2018 51: 111-118.

Sanders JE, Redd CB, Larsen BG, Vamos AC, Brzostowski JT, Hafner BJ, Allyn KJ, McLean JB, Hinrichs P. A novel method for assessing prosthesis use and accommodation practices of people with trans-tibial amputation. J Prosthet Orthot 2018 in press.

Thyssen JP, Linneberg A, Menné T, Johansen JD. The epidemiology of contact allergy in the general population—prevalence and main findings. Contact Dermatitis. Nov. 1, 2007;57(5):287-99.

Baer, Rudolf L. Allergic contact sensitization to iron. Journal of Allergy and Clinical Immunology. 1973;51(1):35-8.

Karakoy M, Gultepe E, Pandey S, Khashab MA, Gracias DH. Silane surface modification for improved bioadhesion of esophageal stents. Applied surface science. Aug. 30, 2014;311:684-9.

Metzler S, Zankovych S, Rauchfuß F, Dittmar Y, Jandt K, Jandt KD, Settmacher U, Scheuerlein H. In vitro analysis of biopolymer coating with glycidoxypropyltrimethoxysilane on hernia meshes. Journal of Biomedical Materials Research Part B: Applied Biomaterials. 2017;105(5):1083-90.

Ogden S, Lewis D, Shapter J. Silane Functionalisation of Iron Oxide Nanoparticles. vol. 7267. 2008.

Caldara M, Colleoni C, Guido E, Re V, Rosace G. Optical monitoring of sweat pH by a textile fabric wearable sensor based on covalently bonded litmus-3-glycidoxypropyltrimethoxysilane coating. Sensors and Actuators B: Chemical. Jan. 1, 2016;222:213-20.

(56) References Cited

OTHER PUBLICATIONS

Guo R, Du X, Zhang R, Deng L, Dong A, Zhang J. Bioadhesive film formed from a novel organic-inorganic hybrid gel for transdermal drug delivery system. European Journal of Pharmaceutics and Biopharmaceutics. Nov. 1, 2011;79(3):574-83.
Wypych G. 2.151.1 Fumed Silica. In: Handbook of Fillers. 2nd ed. New York: Plastics Design Library; 2000.
Razak AHA, Zayegh A, Begg RK, Wahab Y. Foot Plantar Pressure Measurement System: A Review. Sensors (Basel) 2012; 12(7): 9884-9912.
Oberhauser C. Ldc Sensor Design [Internet]. Texas Instruments; 2015 Available from: www.ti.com/lit/snoa930.
Cagle JC, Reinhall PG, Hafner BJ, Sanders JE. Development of standardized material testing protocols for prosthetic liners. J Biomech Engi 2017;139:045001-1-045001-12.
Sanders JE, Lam D, Dralle AJ, Okumura R. Interface pressures and shear stresses at thirteen socket sites on two persons with transtibial amputation. J Rehabil Res Dev. Jan. 1997;34(1):19-43.
Cagle JC, Hafner BJ, Taflin N, Reinhall PG, Sanders JE. Characterization of prosthetic liner product for people with trans-tibial amputation. J Prosthet Orthot. 2017 [epub ahead of print].
Hanspal RS, Fisher K, Nieveen R. Prosthetic socket fit comfort score. Disabil Rehabil 2003; 25: 1278-1280.
Legro MW, Reiber GD, Smith DG, del Aqulia M, Larsen J, Boone D. Prosthesis Evaluation Questionnaire for person with lower limb amputations: Assessing prosthesis-related quality of life. Arch Phys Med Rehabil 1998; 79: 931-938.
Di Leo A. An adjustable fit with a twist of the wrist. In Motion Nov./Dec. 2014; 34-36.
Greenwald RM. Volume management: smart variable geometry socket (SVGS) technology for lower-limb prostheses. JPO 2003; 15(3):107-12.
Legro MW, Reiber G, del Aquila M, Ajax MJ, Boone DA, Larsen JA, Smith DG, Sangeorzan B. Issues of importance reported by persons with lower limb amputations and prostheses. J Rehabil Res Dev 1999; 36(3):155-63.
Marks LJ, Michael JW. Science, medicine, and the future: artificial limbs. BMJ 2001; 323(7315):732-5.
Sanders JE, Cagle JC, Harrison DS, and Karchin A. Amputee stump socks: How does sock ply correlate to sock thickness? Prosthet Orthot Int 2012; 36(1):77-86.
Sanders JE, Hartley TL, Phillips RH, Allyn KJ, Cagle JC, Ciol MA, Harrison DS. Does temporary socket removal affect residual limb fluid volume of trans-tibial amputees? Prosthet Orthot Int 2016; 40(3):320-328.
Sanders JE, Youngblood RT, Hafner BJ, Cagle JC, McLean JB, Redd CB, Dietrich CR, Ciol MA, Allyn KJ. Effects of socket size on metrics of socket fit in trans-tibial prosthesis users. Med Engi Phys 2016a; submitted.
Schaffalitzky E, Gallagher P, Maclachlan M, Wegener ST. Developing consensus on important factors associated with lower limb prosthetic prescription and use. Disabil Rehabil 2012; 34(24):2085-94.
Nandy A, Mondal S, Chakraborty p. Nandi G C. Development of a Robust Microcontroller Based Intelligent Prosthetic Limb. Contemporary Computing; 306/46:452-462, 2012 pp. 445-455.
Razak NAA, Osman NAA, Gholizadeh H, Ali S. Prosthetics socket that incorporates an air splint system focusing on dynamic interface pressure. Biomed Eng Online; 13/108:1-13, 2014.
Gholizadeh H, Osman NAA, Esraghi A, Ali S, Arifin N, Abas W ABW. Evaluation of new suspension system for limb prosthetics. Biomed Eng Online; 13/-:1-13, 2014.
Omasta M, Palousek D, Navrat T, Rosicky J. Finite element analysis for the evaluation of the structural behavior, of a prosthesis for trans-tibial amputees. Medical Engineering and Physics; 34/1:38-45, 2012.
Dumbleton T, Buis AWP, McFayden A, McHugh BF, McKay G, Murray KD, Sexton S. Dynamic interface pressure distributions of two transtibial prosthetic socket concepts. Journal of Rehabilitation Research and Development; 46/3:405-416, 2009.

RevoFit2 Adjustable Prosthetic Socket. https://www.cornerstonepo.com/portfolio-items/revofit2-adjustable-prosthetic-socket/, downloaded Nov. 20, 2020.
Access Prosthetics. Product descriptions for Above Knee Adjustable Sockets. https://accessprosthetics.com/above-knee-adjustable-sockets/. Downloaded Nov. 18, 2020.
Lim Innovations. Product description for Infinite Socket TT-S. https://www.liminnovations.com/infinite-socket-tts/. Downloaded Nov. 18, 2020.
Lim Innovations. Product description for Infinite Socket T/F. https://www.liminnovations.com/infinite-socket-tf/. Downloaded Nov. 18, 2020.
Sanders JE, Severance MR, Allyn KJ.Computer-socket manufacturing error: how much before it is clinically apparent? JRehabilResDev. 2012;49:567-82.
Sanders JE, Cagle JC, Allyn KJ, Harrison DS, Ciol MA. How do activities walking, standing, and resting influence trans-tibial amputee residual limb fluid volume. JRehabilResDev 2014;51(2):201-12.
Youngblood RT, Hafner BJ, Allyn KJ, Cagle JC, Hinrichs P, Redd CB, Vamos AC, Ciol MA, Bean N, Sanders JE. Effects of activity intensity, time, and intermittent doffing on daily limb fluid volume change in people with transtibial amputation. Prosthet Orthot Int 2019;43(1):28-38.
Mercier M, Shirley C, Stafford S, Hitzke S, Byju A, Kevorkian C, Madigan M, Philen M. Fluidic flexible matrix composites for volume management in prosthetic sockets. In Proceedings of the ASME 2014 conference on smart materials, adaptive structures and intelligent systems, Newport, Rhode Island, USA, pp.V002T06A015.
Portnoy S, Yizhar Z, Shabshin N, Itzchak Y, Kristal A, Dotan-Marom Y, Siev-Nerl, Gefen A. Internal mechanical conditions in the soft tissues of a residual limb of a trans-tibial amputee. JBiomech 2008;41:1897-1909.
Portnoy S, Siev-Nerl, Shabshin N, Kristal A, Yizhar Z, Gefen A. Patient-specific analyses of deep tissue loads post-transtibial amputation in residual limbs of multiple prosthetic users. JBiomech2009;42:2686-93.
Portnoy S, van Haare J, Geers RPJ, Kristal A, Siev-Nerl, Seelen HAM, Oomens CWJ, Gefen A. Real-time subject-specific analyses of dynamic internal tissue loads in the residual limb of transtibial amputees.Med Engi Phys 2010;32:312-23.
Sanders JE, Fatone S. Residual limb volume change: systematic review of measurement and management. J Rehabil Res Dev, vol. 48, No. 8, pp. 949-986, 2011.
Ogawa A, Obinata G, Hase K, Dutta A, Nakagawa M. Design of lower limb prosthesis with contact pressure adjustment by MR fluid. Proceedings of the 30th Annual International IEEE EMBS Conference, Vancouver, British Columbia, Canada, Aug. 20-24, 2008.
Wheeler JW, Mazumdar A, Marron L, Dullea K, Sanders J, Allyn K. Development and Amputee Validation of Pressure and Shear Sensing Liner for Prosthetic Sockets. IEEE Engineering in Medicine and Biology Society, Orlando, FL, USA, 2016.
Pirouzi G, Abu Osman NA, Oshkour AA, Ali S, Gholizadeh H, Wan Abas WAB. Development of an air pneumatic suspension system for trans-tibial prostheses. Sensors (Basel), vol. 14, No. 9, pp. 16754-65, 2014.
Candrea D, Sharma A, Osborn L, Gu Y, Thakor N. An adaptable prosthetic socket: Regulating independent air pladders through closed-loop control. IEEE International Symposium on Circuits and Systems (ISCAS), Baltimore, MD, USA, pp. 1-4, 2017.
Carrigan W, Nothnagle C, Savant p. Gao F, Wijesundara MJ. Pneumatic actuator inserts for interface pressure mapping and fit improvement in lower extremity prosthetics. Proceedings of the IEEE International Conference in Biorobotics, pp. 574-579, 2016.
McLean JB, Redd CB, Larsen BG, Garbini JL, Brzostowski JT, Hafner BJ, Sanders JE. Socket size adjustments in people with trans-tibial amputation: Effects on residual limb fluid volume and limb-socket distances. Clin Biomech, 2019, in press.
Sanders JE, Larsen BG, McLean JB, Brzostowski JT, Gurrey CJ, Hafner BJ, Garbini JL, Hinrichs P, Allyn KJ, Youngblood RT. Incremental socket size adjustments during ambulation: effects on residual limb fluid volume. American Academy of Orthotists &

(56) References Cited

OTHER PUBLICATIONS

Prosthetists 44th Academy Annual Meeting and Scientific Symposium, Workshop on Methods for Assessing Socket Fit, New Orleans, LA, USA, 2018.
Sanders JE, Garbini JL, McLean JB, Hinrichs P, Predmore TJ, Brzostowski JT, Redd CB, Cagle JC. A motor-driven, adjustable prosthetic socket operated using a mobile phone app: A technical note. Med Eng Phys, 2018, submitted.
Weathersby EJ, Cagle JC, Larsen BG, Henrikson KM, Sanders JE. Development of a magnetic composite material for measurement of residual limb displacements in prosthetic sockets. J Rehabil Assist Technol Eng, vol. 5, 2018.
Henrikson KM, Weathersby EJ, Larsen BG, Cagle JC, McLean JB, Sanders JE. An Inductive Sensing System to Measure In-Socket Residual Limb Displacements for People Using Lower-Limb Prostheses. Sensors (Basel), vol. 18, No. 11, Nov. 9, 2018.
Vamos AC, Gurrey CJ, Cagle JC, Brzostowski JT, McLean JB, Sanders JE. An algorithm to calculate socket volume changes of adjustable sockets for transtibial prosthesis users. J Prosthet Orthot, 2020, in press.
Darter BJ, Sinitski K, Wilken JM. Axial bone-socket displacement for persons with a traumatic transtibial amputation: The effect of elevated vacuum suspension at progressive body-weight loads. Prosthet Orthot Int, vol. 40, No. 5, pp. 552-557 2016.
Wernke M, McGough J, Albury A, Denune J, Doddroe C, Colvin J, Rink C, Sen C, Hendershot B, Dearth C. Multiaxial in-socket movement and its relationship to fit. American Academy of Orthotists & Prosthetists 44th Academy Annual Meeting and Scientific Symposium, New Orleans, LA, USA, 2018.
Mitton K, Kulkarni J, Dunn KW, Ung AH. Fluctuating residual limb volume accommodated with an adjustable, modular socket design: A novel case report. Prosthet Orthot Int, vol. 41, No. 5, pp. 527-531, 2017.
Kahle JT, Klenow TD, Highsmith MJ. Comparative effectiveness of an adjustable transfemoral prosthetic interface accommodating volume fluctuation: case study. Technol Innov, vol. 18, pp. 175-183, 2016.
Dillingham T, Kenia J, Shofer F, Marschalek J. A prospective assessment of an adjustable, immediate fit, transtibial prosthesis. PM&R, 2019 [epub ahead of print].
Beghaei-Nejad M, Mendoza DS, Zou Z, Radiom S, Gielen G, Zheng LR, Tenhunen H. A Remote-Powered RFID Tag with 10Mb/s UWB Uplink and −18.5dBm Sensitivity UHF Downlink in 0.18 μm CMOS. IEEE International Solid-State Circuits Conference 2009, Session 11; TD: Trends in Wireless Communications, 11.2.
Goršič M, Kamnik R, Ambrožič L, Vitiello N, Lefeber D, Pasquini G, Munih M. Online Phase Detection Using Wearable Sensors for Walking with a Robotic Prosthesis. Sensors 2014;14: 2776-2794.
Griffin J, Durgin G. Multipath Fading Measurements for Multi-Antenna Backscatter RFID at 5.8 GHz. 2009 IEEE International Conference on RFID, 322-329.
Juang H, Farahanipad F, Singk AK. A Stacked Dual-Frequency Microstrip Patch Antenna for Simultaneous Shear and Pressure Displacement Sensing. IEEE Sensors J, vol. 17, No. 24, Dec. 15, 2017.
Qiu S, Wang Z, Zhao H, Hu Huosheng. Using Distributed Wearable Sensors to Measure and Evaluate Human Lower Limb Motions. IEEE Transactions on Instrumentation and Measurement, vol. 65, No. 4, Apr. 2016.
Salazar-Salgado S, Rendón-Vélez E. Measuring Displacement Within a Transfemoral Socket Using Marker-based Optical Tracking System: Static Tests. Proceedings of the ASME 2017 International Mechanical Engineering Congress and Exposition, Tampa, Florida, Nov. 3-9.
Valenta C, Durgin G. Rectenna Performance Under Power-optimized Waveform Excitation. 2013 IEEE International Conference on RFID, 237-244.
Zhang R, Ho CK. MIMO Broadcasting for Simultaneous Wireless Information and Power Transfer. IEEE Communications Society, 2011 IEEE Globecom Proceeings.

\* cited by examiner

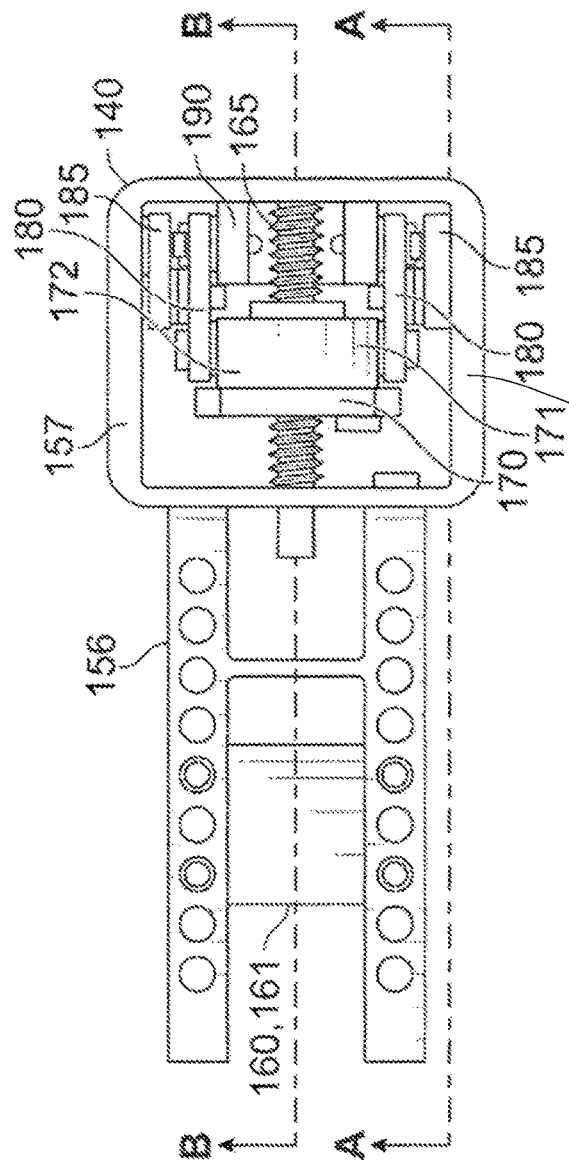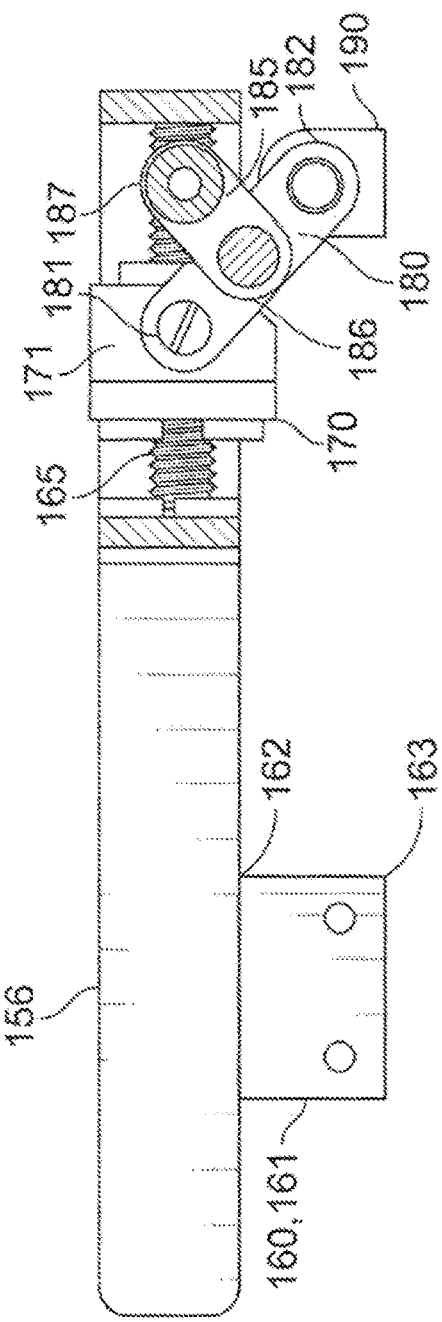
FIG. 5
FIG. 6

MOTORIZED ADJUSTABLE SOCKET FOR AMPUTEE PROSTHESIS USERS AND METHODS FOR USE THEREOF

CROSS-REFERENCE TO RELATED APPLICATION

This application claims the benefit of the filing date of U.S. Provisional Patent Application Ser. No. 62/841,655, filed May 1, 2019, which is hereby incorporated by reference in its entirety.

STATEMENT OF FEDERALLY SPONSORED RESEARCH AND DEVELOPMENT

This invention was made with government support under Grant No. R01 HD060585, awarded by the National Institutes of Health and Grant No. W81XWH-16-C-0020, awarded by the U.S. Army Medical Research and Materiel Command. The government has certain rights in the invention.

BACKGROUND

People wearing prosthetic limbs often experience socket fit problems because of residual limb volume loss. Socket fit is reported as the single-most important issue faced by people with limb amputation. Management of socket fit (e.g. adding socks to accommodate volume loss) is challenging for many trans-tibial prosthesis users. Some users, especially people who have recently had a limb amputated or people with poor limb sensation, find it difficult to identify when a socket size change is needed. Once a need for socket-size accommodation is identified, some users consider the inconvenience of conducting the adjustment not worth the trouble. People wearing pants, for example, must remove them to change socks, which interrupts their activity, is time consuming, and may not be possible in certain social environments. Finally, determining the amount of socket-size adjustment to make is also an issue (e.g., the sock thickness that should be added). Adding too much sock thickness may occlude blood flow, accentuate volume loss, and detrimentally affect health of limb tissues. Adding insufficient sock thickness may not resolve the socket fit problem and risk a fall.

Sockets that adjust their size using a passive pressure-driven mechanism or based on interface stress measurement from sensors on the prosthesis have been pursued by several investigators. Sockets have been created that adjust liquid within bladders or tubes either affixed to the socket or embedded within prosthetic liners. Air bladders have also been used to adjust socket size.

SUMMARY

In a first aspect, an example apparatus for automatically adjusting a socket size of a prosthesis is disclosed. The apparatus includes (a) the prosthesis having a socket configured to receive a liner arranged over a limb, (b) a first opening in a wall of the socket, (c) a first panel aligned with the first opening, (d) a first actuator coupled to the first panel and to the prosthesis, wherein the first actuator is configured to advance and retract the first panel through the first opening, (e) a first sensor coupled to the wall of the socket and configured to obtain limb-to-socket gap data corresponding to a distance between the limb and the wall of the socket, and (f) a processor communicatively coupled to the first actuator and to the first sensor, wherein the processor is configured (i) to receive the limb-to-socket gap data, (ii) to determine a socket-size adjustment based on the limb-to-socket gap data and a predetermined socket-fit value, (iii) to generate a command with the socket-size adjustment, and (iv) to send the command with the socket-size adjustment to the first actuator to advance or retract the first panel through the first opening.

In a second aspect, an example method for automatically adjusting a socket size of a prosthesis using an apparatus according to the first aspect is disclosed. The method includes (a) receiving, via the processor, the limb-to-socket gap data from the first sensor, (b) determining, via the processor, a socket-size adjustment based on the limb-to-socket gap data from the first sensor and the predetermined socket-fit value, (c) generating, via the processor, the command with the socket-size adjustment, and (d) sending, via the processor, the command with the socket-size adjustment to the first actuator to advance or retract the first panel through the first opening.

In a third aspect, an example non-transitory computer-readable medium is disclosed. The computer readable medium has stored thereon program instructions that upon execution by a processor, cause performance of a set of acts including (a) receiving the limb-to-socket gap data from the first sensor, (b) determining a socket-size adjustment based on the limb-to-socket gap data from the first sensor and the predetermined socket-fit value, (c) generating the command with the socket-size adjustment, and (d) sending the command with the socket-size adjustment to the first actuator to advance or retract the first panel through the first opening.

BRIEF DESCRIPTION OF THE DRAWINGS

The foregoing aspects and many of the attendant advantages of the apparatus and methods of the disclosure will become more readily appreciated with reference to the following detailed description, when taken in conjunction with the accompanying drawings, wherein:

FIG. 5 is a rear view of the actuator according to one example implementation;

FIG. 6 is a cross-sectional side view of the actuator along line A-A in FIG. 5;

Figure 1:
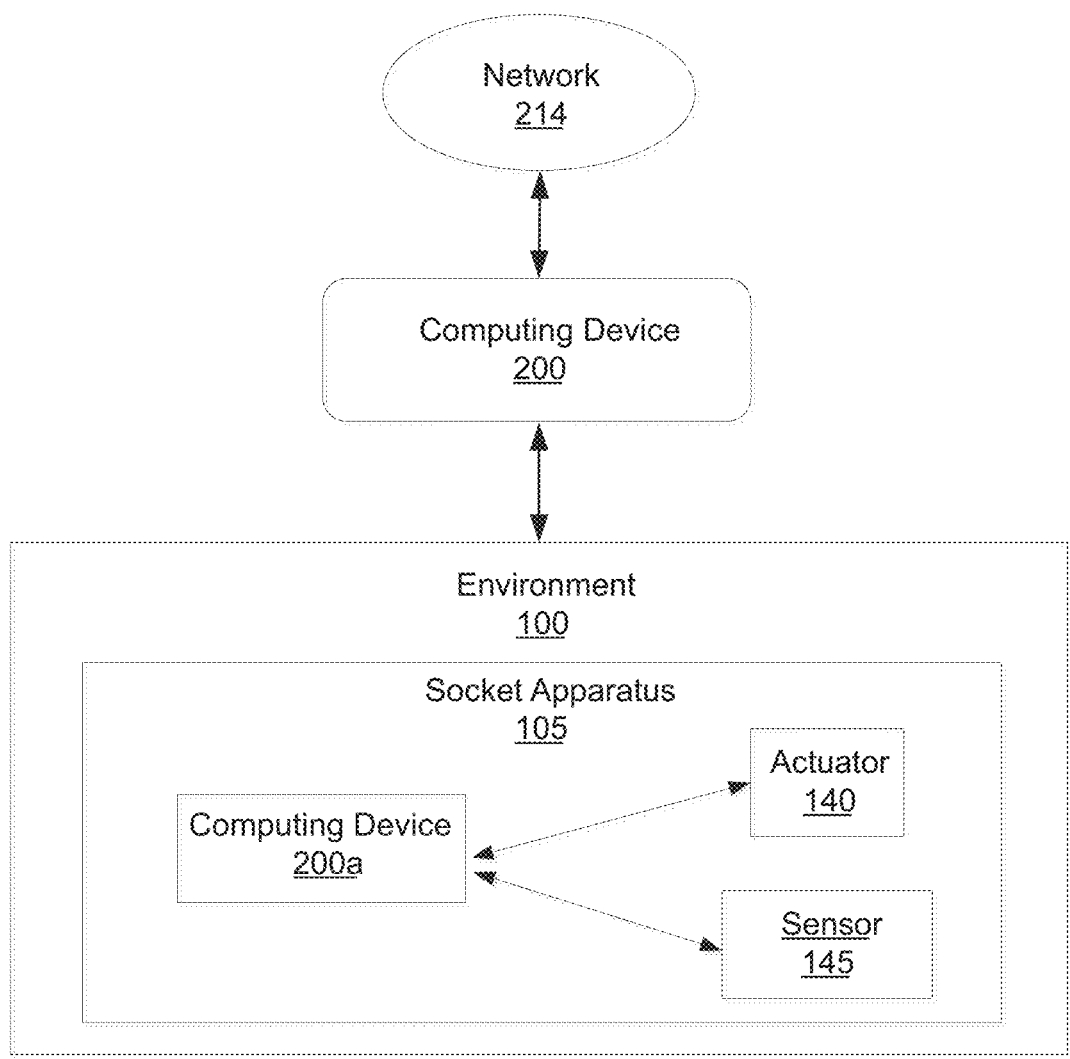
FIG. 1 is a functional block diagram of a system, according to one example implementation.

The drawings are provided for the purpose of illustrating examples, but it is understood that the examples are not limited to the arrangements and instrumentalities shown in the drawings.

DETAILED DESCRIPTION

I. Overview

Implementations of an apparatus and methods described herein can advantageously provide a socket for a prosthetic that adjusts socket size automatically upon a detection of deteriorating socket fit with a user's limb to maintain a proper fit and stabilize limb volume. The disclosed auto-adjusting socket apparatus and methods also reduce residual limb health complications from poor socket fit. The apparatus and methods relieve users of the burden of continually sensing if their socket fit has deteriorated, deciding what adjustment to make, and effecting a socket size change. Users may instead focus on other aspects of their life. The auto-adjusting socket apparatus and methods should enhance independence, improve limb health, and enrich patient quality of life.

The automatic socket-size adjustments provided by the socket apparatus and methods disclosed herein may also optionally operate in three different modes, namely for walking, for low activity (i.e., short bouts of walking combined with periods of standing), and for sitting or rest. As recognized in the present disclosure, effective adjustment in terms of both comfort and maintenance of limb volume requires both socket enlargement and reduction. Reducing an oversized socket reduces risk of discomfort and soft tissue injury and ensures stable limb-socket coupling during ambulation. Enlarging an undersized socket relieves interface stresses on soft tissues, reducing discomfort and risk of injury, and facilitates limb fluid volume recovery during ambulation. Periodic socket enlargement during rest also facilitates the recovery of limb fluid volume and its retention during subsequent activity. By harnessing feedback from various sensors of the apparatus, the processor may determine the operating mode based on user activity and then responsively determines the frequency and degree of socket-size adjustments.

II. Example Architecture

FIG. 1 is a block diagram showing an environment 100 that may include outdoor space with varying terrain or an indoor space such as an office building or that includes a treadmill or furniture for rest. The environment 100 includes or involves, for example, an apparatus 105 for automatic socket size adjustment of a prosthesis that includes an actuator 140 and at least one sensor 145, as shown in detail in FIGS. 3-10 and described below. A user wearing the apparatus may be engaged in walking, high activity, low activity, sitting or rest in environment 100. Method 300 in FIG. 11 described below shows an implementation of a method that can be used within this environment 100 using apparatus 105.

Figure 2:
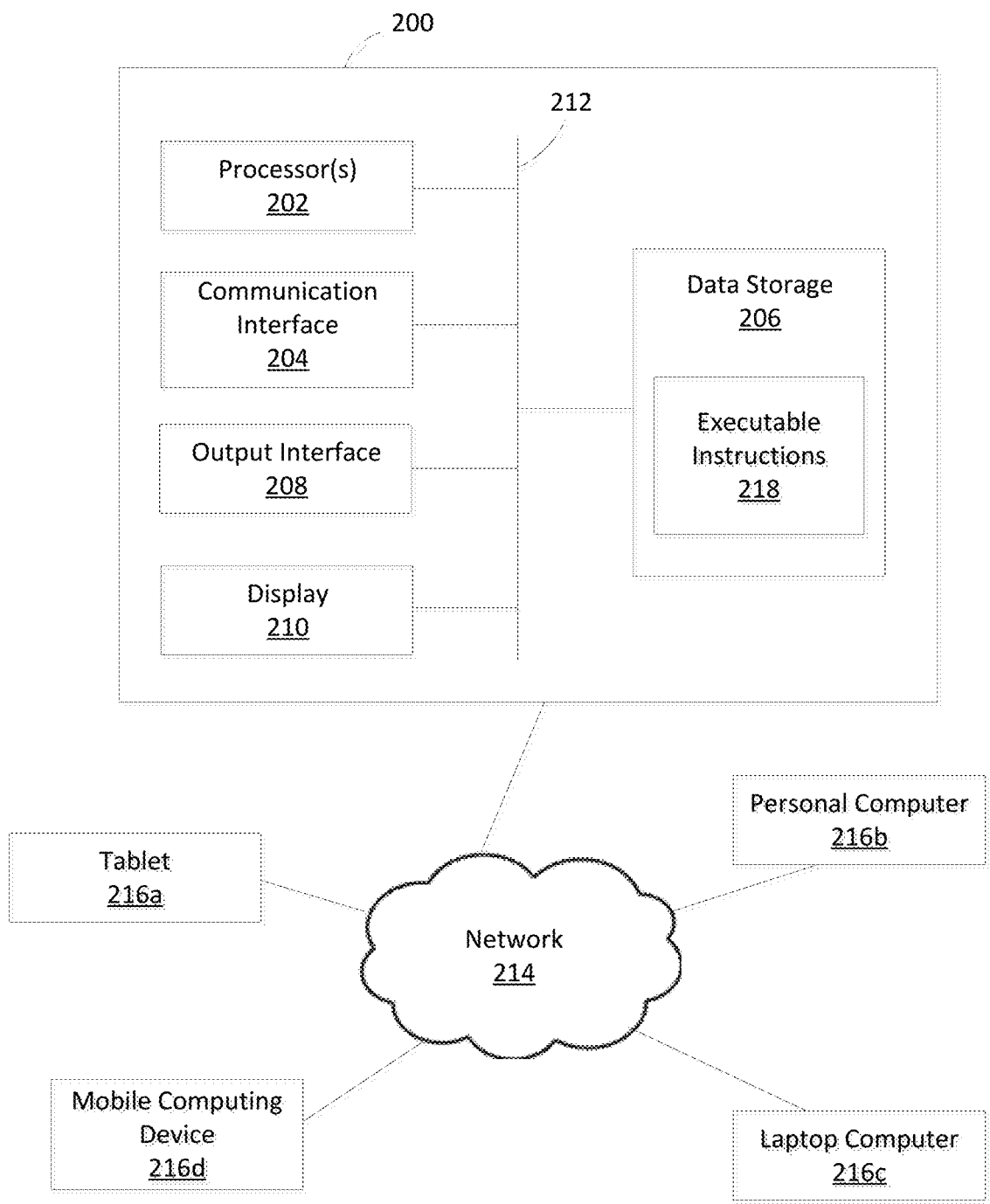
FIG. 2 is a block diagram of a computing device and a computer network, according to an example implementation.

FIG. 2 is a block diagram illustrating an example of a computing device 200, according to an example implementation, that is configured to interface with environment 100, either directly or indirectly. The computing device 200 may be used to perform functions of the method shown in FIG. 11 and described below. In particular, computing device 200 can be configured to perform one or more functions, including, but not limited to, determining a socket-size adjustment and thereby adjusting a socket-size of the apparatus 105, for example. The computing device 200 has a processor(s) 202, and also a communication interface 204, data storage 206, an output interface 208, and a display 210 each connected to a communication bus 212. The computing device 200 may also include hardware to enable communication within the computing device 200 and between the computing device 200 and other devices (e.g. not shown). The hardware may include transmitters, receivers, and antennas, for example.

The communication interface 204 may be a wireless interface and/or one or more wired interfaces that allow for both short-range communication and long-range communication to one or more networks 214 or to one or more remote computing devices 216 (e.g., a tablet 216a, a personal computer 216b, a laptop computer 216c and a mobile computing device 216d, for example). Such wireless interfaces may provide for communication under one or more wireless communication protocols, such as Bluetooth, Wi-Fi (e.g., an institute of electrical and electronic engineers (IEEE) 802.11 protocol), Long-Term Evolution (LTE), cellular communications, near-field communication (NFC), and/or other wireless communication protocols. Such wired interfaces may include Ethernet interface, a Universal Serial Bus (USB) interface, or similar interface to communicate via a wire, a twisted pair of wires, a coaxial cable, an optical link, a fiber-optic link, or other physical connection to a wired network. Thus, the communication interface 204 may be configured to receive input data from one or more devices and may also be configured to send output data to other devices.

The communication interface 204 may also include a user-input device, such as a keyboard, a keypad, a touch screen, a touch pad, a computer mouse, a track ball and/or other similar devices, for example.

The data storage 206 may include or take the form of one or more computer-readable storage media that can be read or accessed by the processor(s) 202. The computer-readable storage media can include volatile and/or non-volatile storage components, such as optical, magnetic, organic or other memory or disc storage, which can be integrated in whole or in part with the processor(s) 202. The data storage 206 is considered non-transitory computer readable media. In some examples, the data storage 206 can be implemented using a single physical device (e.g., one optical, magnetic, organic or other memory or disc storage unit), while in other examples, the data storage 206 can be implemented using two or more physical devices.

The data storage 206 thus is a non-transitory computer readable storage medium, and executable instructions 218 are stored thereon. The instructions 218 include computer executable code. When the instructions 218 are executed by the processor(s) 202, the processor(s) 202 are caused to perform functions. Such functions include, but are not limited to, (i) receiving limb-to-socket gap data, (ii) determining a socket-size adjustment based on the limb-to-socket gap data and a predetermined socket-fit value, (iii) to generating a command with the socket-size adjustment, (iv) sending the command with the socket-size adjustment to the first actuator to advance or retract the first panel through the first opening to thereby adjust socket size, (v) receiving limb-depth data, (vi) determining the socket-size adjustment further based on the limb-depth data to thereby adjust socket size, (vii) determining a current operating mode is one of a walking mode, a high activity mode, a low activity mode and a rest mode based on the limb-to-socket gap data and the limb-depth data and (viii) determining the socket-size adjustment further based on the current operating mode, for example.

The processor(s) 202 may be a general-purpose processor or a special purpose processor (e.g., digital signal processors, application specific integrated circuits, etc.). The processor(s) 202 may receive inputs from the communication interface 204, and process the inputs to generate outputs that are stored in the data storage 206 and output to the display 210. The processor(s) 202 can be configured to execute the executable instructions 218 (e.g., computer-readable program instructions) that are stored in the data storage 206 and are executable to provide the functionality of the computing device 200 described herein.

The output interface 208 outputs information to the display 210 or to other components as well. Thus, the output interface 208 may be similar to the communication interface 204 and can be a wireless interface (e.g., transmitter) or a wired interface as well. The output interface 208 may send commands to one or more controllable devices, for example.

The computing device 200 shown in FIG. 2 may also be representative of a local computing device 200a in environment 100, for example, in communication with the apparatus 105, including the actuator 140 and at least one sensor 145. This local computing device 200a may perform one or more of the steps of the method 300 described below, may receive input from a user, may receive data from sensors in the apparatus 105 and/or may send sensor data and user input to computing device 200 to perform all or some of the steps of method 300.

Figure 11:
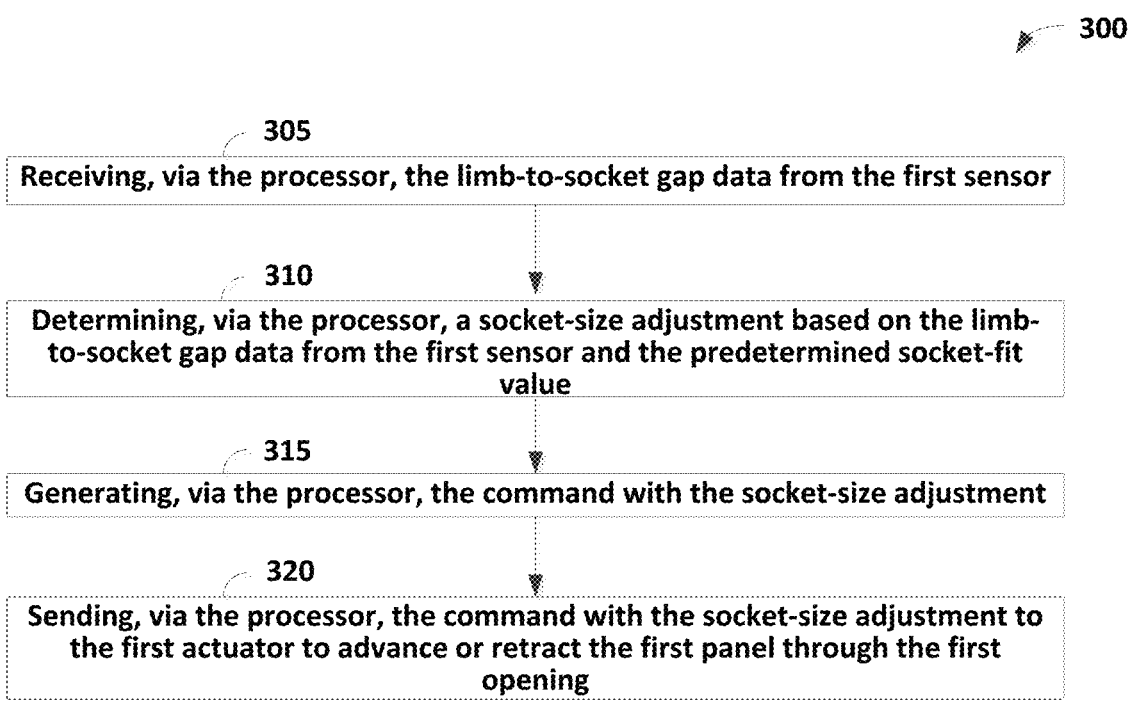
FIG. 11 shows a flowchart of a method, according to an example implementation.

FIG. 11 shows a flowchart of an example method 300 to control socket-size adjustment of the apparatus 105. Method 300 shown in FIG. 11 presents an example of a method that could be used with the computing device 200 of FIG. 2, for example. In some instances, components of the apparatus 105 may be configured to perform the functions such that the components are configured and structured with hardware and/or software to enable such performance. Components of the systems may be arranged to be adapted to, capable of, or suited for performing the functions, such as when operated in a specific manner. Method 300 may include one or more operations, functions, or actions as illustrated by one or more of blocks 305-320. Although the blocks are illustrated in a sequential order, some of these blocks may also be performed in parallel, and/or in a different order than those described herein. Also, the various blocks may be combined into fewer blocks, divided into additional blocks, and/or removed based upon the desired implementation.

It should be understood that for this and other processes and methods disclosed herein, flowcharts show functionality and operation of one possible implementation of the present examples. In this regard, each block may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium may include non-transitory computer readable medium or memory, for example, such as computer-readable media that stores data for short periods of time such as register memory, processor cache and Random Access Memory (RAM). The computer readable medium may also include non-transitory media, such as secondary or persistent long-term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example.

In addition, each block in FIG. 11, and within other processes and methods disclosed herein, may represent circuitry that is wired to perform the specific logical functions in the process. Alternative implementations are included within the scope of the examples of the present disclosure in which functions may be executed out of order from that shown or discussed, including substantially concurrent or in reverse order, depending on the functionality involved, as would be understood by those reasonably skilled in the art.

III. Example Apparatus

Figure 3:
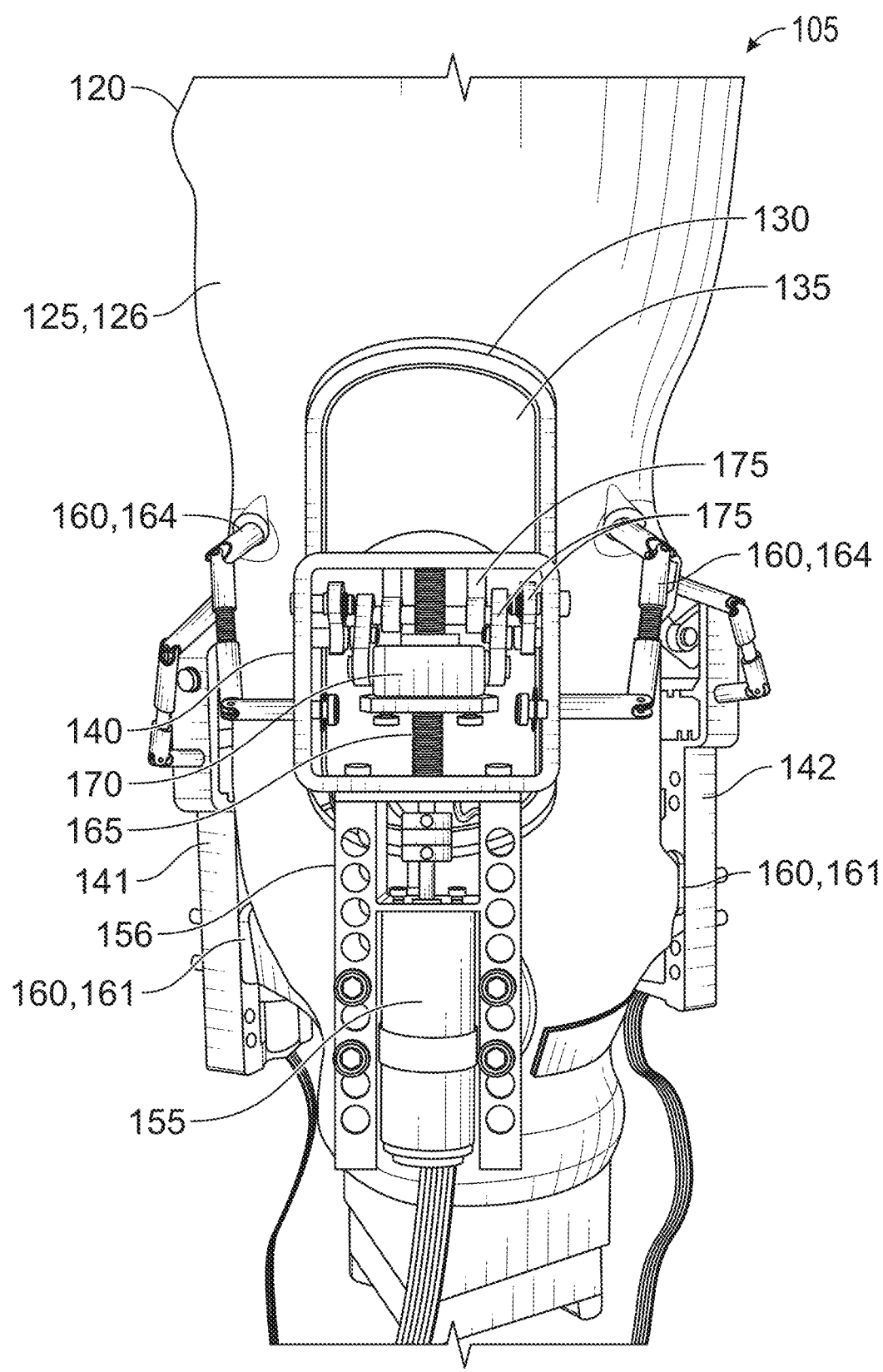
FIG. 3 is a rear posterior view of the apparatus according to one example implementation.
Figure 4:
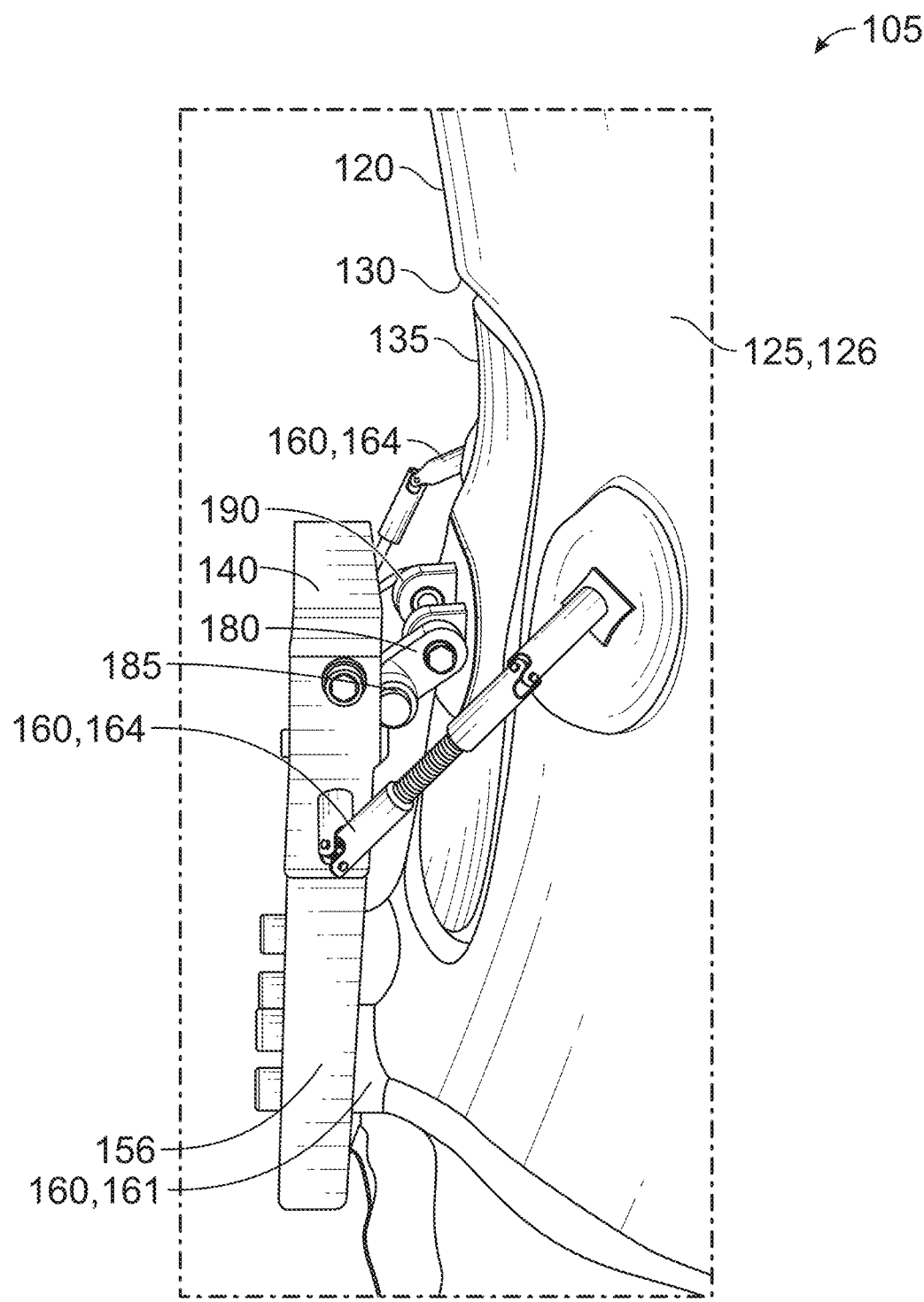
FIG. 4 is a side detail view of the apparatus according to FIG. 1 showing an actuator and moveable panel.
Figure 7:
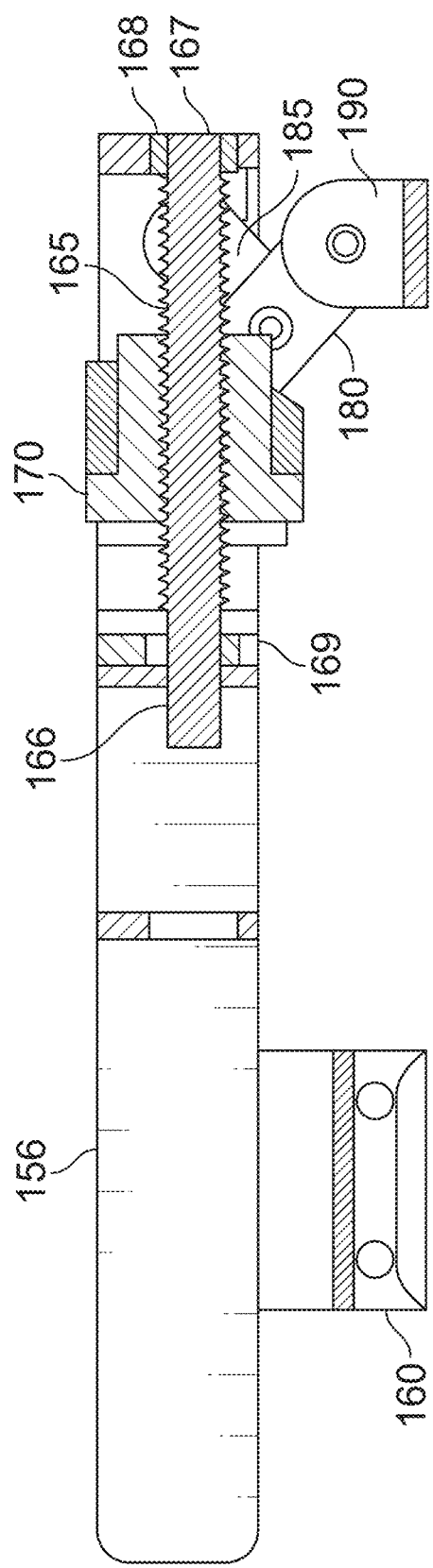
FIG. 7 is a cross-sectional side view of the actuator along line B-B in FIG. 5.
Figure 8:
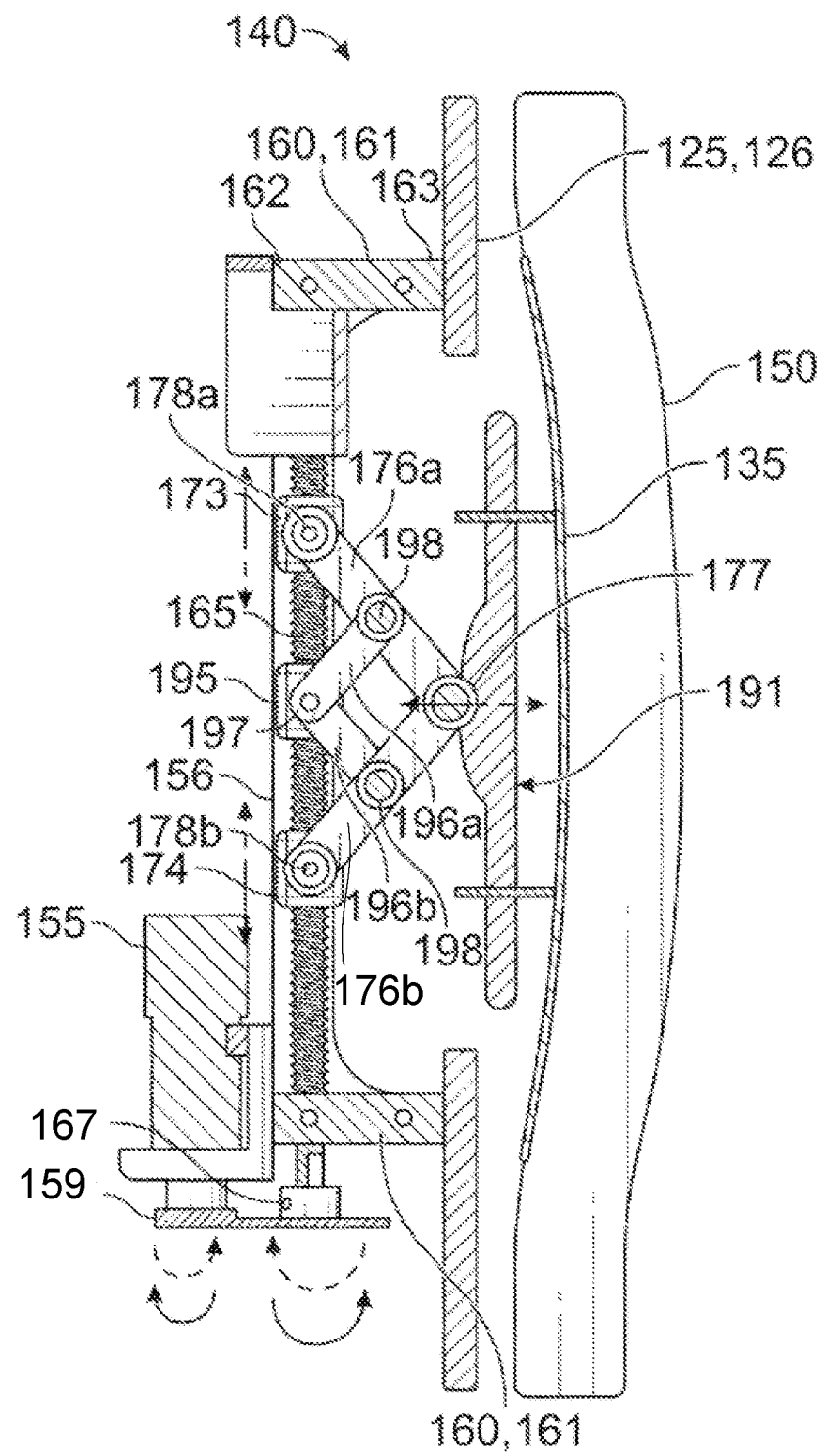
FIG. 8 is a side view of the actuator according to another example implementation.
Figure 9:
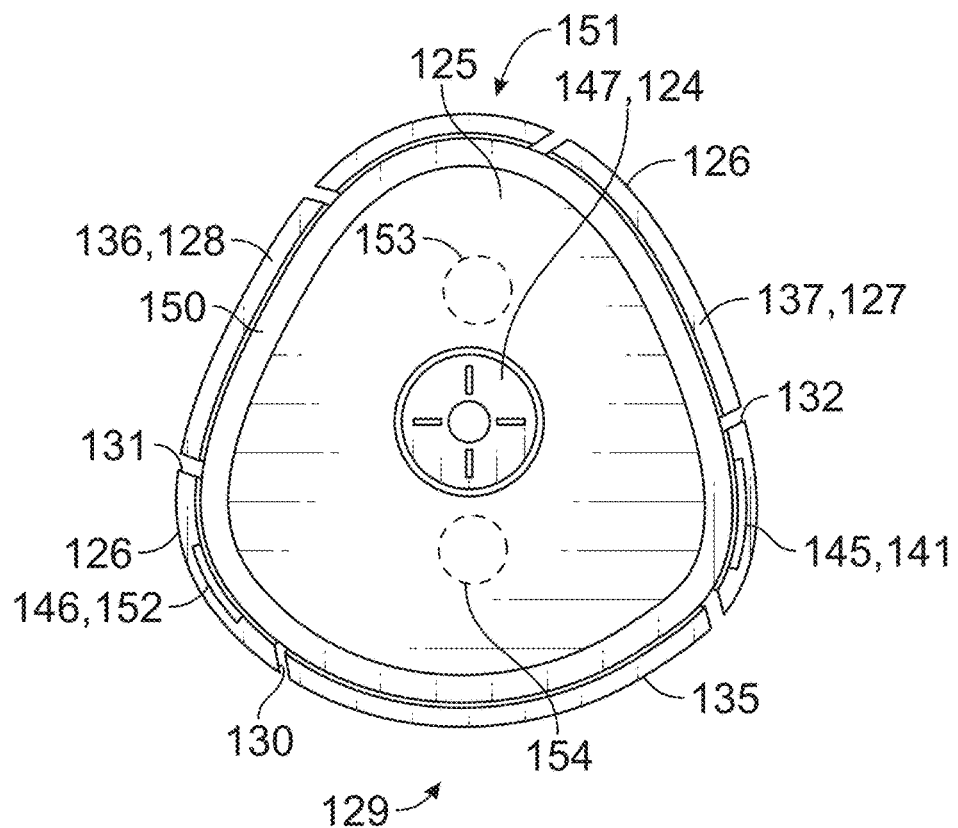
FIG. 9 is a top cross-sectional view of the apparatus according to one example implementation.

In a first aspect, shown in FIGS. 3-10, an apparatus 105 for automatically adjusting a socket size of a prosthesis 120, includes the prosthesis 120 having a socket 125 configured to receive a liner 150 arranged over a limb. The apparatus 105 also includes a first opening 130 provided in a wall 126 of the socket and a first panel 135 that is aligned with the first opening 130. In one optional implementation, the first opening 130 and the first panel 135 are arranged at a posterior location 129 on the wall 126 of the socket 125, as shown in FIGS. 3 and 9. A first actuator 140 is coupled to the first panel 135 and to the prosthesis 120. The first actuator 140 is configured to advance and retract the first panel 135 through the first opening 130. The technical effect of this arrangement is to increase or decrease the effective socket size of the prosthesis to maintain a proper fit with a user's limb and to stabilize limb volume. The first actuator 140 is discussed in further detail below.

In one optional implementation, the apparatus 105 may include a second opening 131 in the wall 126 of the socket 125 and a second panel 136 aligned with the second opening 131. In this arrangement, the second opening 131 and the second panel 136 are arranged at an anterior-lateral location 128 on the wall 126 of the socket 125. A second actuator 141 is coupled to the second panel 136 and to the prosthesis 120. The second actuator 141 is configured to advance and retract the second panel 136 through the second opening 131. The apparatus 105 may further include a third opening 132 in the wall 126 of the socket 125 and a third panel 137 aligned with the third opening 132. The third opening 132 and the third panel 137 are arranged at an anterior-medial location 127 on the wall 126 of the socket 125. And a third actuator 142 coupled to the third panel 137 and to the prosthesis 120. The third actuator 142 is configured to advance and retract the third panel 137 through the third opening 132.

The apparatus 105 further includes a first sensor 145 coupled to the wall 126 of the socket 125 and configured to obtain limb-to-socket gap data corresponding to a distance between the limb and the wall of the socket. As used herein, "limb-to-socket gap data" includes a sensed or detected distance (SD) or gap between the first sensor and a liner 150 arranged over a limb that is disposed in the socket 125, as well as a corresponding time of detection. This limb-to-socket gap data may also be obtained continuously and may be stored on a remote computing device, in one example implementation. In one optional implementation, the first sensor 145 is an inductive sensor. In a further optional implementation, the first sensor 145 is arranged at a posterior-medial mid-limb location 141, or alternatively in a posterior-lateral mid-limb location 152. In operation, a user wears a liner 150 on the limb. The liner 150 has iron powder incorporated therein that may be detected by the first sensor 145 to determine a distance between the liner 150 (i.e., the limb) and the first sensor 145. In one implementation, the liner 150 is an elastomer having an iron concentration ranging from about 80% to 85% by weight with the iron contained within the outer 1 mm of the elastomer.

In one optional implementation, the apparatus 105 includes a second sensor 146 coupled to the wall 126 of the socket 125 and configured to obtain the limb-to-socket gap data. This limb-to-socket gap data from the second sensor 146 may be used to audit the limb-to-socket gap data from the first sensor 145 to improve accuracy of the socket-fit adjustment determination and to identify any abnormal measurements in the sensed distance. In one implementation, the second sensor 146 is an inductive sensor. And the second sensor 146 may be arranged at an anterior mid-limb location 151, a posterior-lateral mid-limb location 152, an anterior-distal location 153, a posterior-distal location 154, or an anterior-proximal location (located near the top of the socket on the anterior side shown in FIG. 9). When both the first sensor and the second sensor obtain limb-to-socket gap data, the processor 202 may calculate and use the mean value for a given time to determine the effective distance between the liner 150 and the wall 126 of the socket 125. In one specific example implementation, the first sensor 145 is arranged at a posterior-medial mid-limb location 141 and the second sensor 146 is arranged in a posterior-lateral mid-limb location 152. In other optional implementations, various other sensors may be coupled to the wall 126 of the socket 125 to obtain limb-to-socket gap data for use in a determination of a socket-size adjustment and/or for use in a determination that a current operating mode is one of a walking mode, a high activity mode, a low activity mode or a rest mode. For example, a third sensor in a distal anterior location in the wall 126 of the socket 125 may obtain data for the processor 202 to determine a current operating mode is a walking mode. And the processor further determines a socket-fit adjustment based on thresholds and step-size adjustments associated with the walking mode.

Still further, the apparatus 105 includes a processor 202 communicatively coupled to the first actuator 140 and to the first sensor 145. As used herein, "communicatively coupled" refers to both a wired or wireless connection, as discussed in more detail in the Example Architecture section above.

The processor 202 is configured (i) to receive the limb-to-socket gap data from the first sensor 145, (ii) to determine a socket-size adjustment based on the limb-to-socket gap data and a predetermined socket-fit value, (iii) to generate a command with the socket-size adjustment, and (iv) to send the command with the socket-size adjustment to the first actuator to advance or retract the first panel through the first opening. In example implementations, multiple panels in the wall 126 of the socket 125, the first panel 135, the second panel 136, and the third panel 137 may be adjusted the same amount or different amounts according to predetermined settings. These predetermined settings may be provided by a trained practitioner and may be specific to a given user. In one implementation, these predetermined settings may be modified in response to feedback received from a remote computing device 216.

In operation, the processor 202 continuously receives limb-to-socket gap data based on a set time step and iteratively determines a socket-size adjustment to thereby effect automatic adjustment of the socket size. The time step may be adjusted based on the current operating mode (e.g., walking, high activity, low activity, and rest) as determined by the processor 202 or as provided by a user using a remote computing device 216. In one optional implementation, the processor 202 is communicatively coupled to the second sensor 150 to receive additional limb-to-socket gap data, as discussed above, and may use a mean value, for example, of the data obtained from the first sensor 145 and the second sensor 146.

The predetermined socket-fit value may be based on the socket fit metric (SFM) and/or input provided by the user for a preferred socket fit. The predetermined socket-fit value may be further set based on whether the current operating mode is one of a walking mode, a high activity mode, a low activity mode or a rest mode.

In one implementation, the first actuator 140 includes an electric motor 155. In various embodiments, the electric motor 155 may be operated in two directions to effect either an increase or a decrease in socket-size adjustment. At a high level, in one optional implementation, the electric 155 motor may be used to spool and unspool cables coupled to the first panel 135 anchored on one end to the socket wall and coupled to the electric motor 155 at the other end. In one implementation, the cables may be disposed within channels formed in the wall 126 of the socket 125 and may also be coupled to the second and third panels 136, 137.

As shown in FIG. 8, in another implementation of the first actuator 140, a sleeve 195 is disposed on the lead screw 165. The sleeve 195 is not threaded and is held in place by the plurality of linkages 175. In addition, the at least one travel nut 170 includes a first travel nut 173 and a second travel nut 174 arranged on opposing sides of the sleeve 195. The first travel nut 173 and the second travel nut 174 are arranged such that rotation of the lead screw 165 in a first direction causes the first travel nut 173 and the second travel nut 174 to move toward each other and toward the sleeve 195 to advance the panel mount forward to reduce socket size. Similarly, rotation in a second direction causes the first travel nut 173 and the second travel nut 174 to move away from each other and the sleeve 195 thereby retracting the panel mount 191 rearward to increase socket size. In one optional embodiment, the electric motor 155 and the lead screw 165 are coupled together via gears 159.

As shown in FIGS. 3-7, in one implementation of the first actuator 140, the plurality of linkages 175 includes a pair of first linkages 180 and a pair of second linkages 185. The pair of first linkages 180 is rotatably coupled at first ends 181 to opposing sides 171, 172 of the at least one travel nut 170 and rotatably coupled at second ends 182 to opposing sides of a panel mount 190. And panel mount 190 is coupled to the first panel 135. The pair of second linkages 185 is rotatably coupled at first ends 186 to the pair of first linkages 180 and rotatably coupled at second ends 187 to opposing sides 157, 158 of the frame 156. In one implementation, a length of the pair of first linkages 180 is greater than a length of the pair of second linkages 185. In operation, as the at least one travel nut 170 is advanced toward the second end 167 of the lead screw, the pair of first and second linkages 175, 185 rotatably cooperate to cause the panel mount 190 to advance forward to reduce socket size. Likewise, as the at least one travel nut 170 is advanced toward the first end 166 of the lead screw, the pair of first and second linkages 175, 185 rotatably cooperate to cause the panel mount 190 to retract rearward to increase socket size.

In addition, as shown in FIGS. 3-7, in one optional implementation, the plurality of supports 160 includes (i) a support block 161 having a first end 162 coupled to the frame 156 and a second end 163 extending from the frame 156 and coupled to the prosthesis 120 below the first opening 130 and (ii) a pair of arms 164 arranged on opposing sides of the frame 156 and coupled to the prosthesis 120 on opposing sides of the first opening 130.

As shown in FIG. 8, in another implementation of the first actuator 140, a sleeve 195 is disposed on the lead screw 165. The sleeve 195 is not threaded and is held in place by the plurality of linkages 175. In addition, the at least one travel nut 170 includes a first travel nut 173 and a second travel nut 174 arranged on opposing sides of the sleeve 195. The first travel nut 173 and the second travel nut 174 are arranged such that rotation of the lead screw 165 in a first direction causes the first travel nut 173 and the second travel nut 174 to move toward each other and toward the sleeve 195 to advance the panel mount forward to reduce socket size. Similarly, rotation in a second direction causes the first travel nut 173 and the second travel nut 174 to move away from each other and the sleeve 195 thereby retracting the panel mount 191 rearward to increase socket size. In one optional embodiment, the electric motor 155 and the lead screw 165 are coupled together via gears 157.

In the example of FIG. 8, the plurality of linkages 175 include a pair of first linkages 176a,b and a pair of second linkages 196a,b. The pair of first linkages 176a,b are each rotatably coupled at a first end 177 to the first panel 135, optionally via a panel mount 191, and one of the pair of first linkages 176a is rotatably coupled at a second end 178a to the first travel nut 173 and the other of the pair of first linkages 176b is rotatably coupled at a second end 178b to the second travel nut 174. The pair of second linkages 196a,b are each rotatably coupled at a first end 197 to the sleeve 195 and one of the pair of second linkages 196a is rotatably coupled at a second end 198 to one of the pair of the first linkages 176a and the other of the pair of second linkages 196b is rotatably coupled at a second end 198 to the other of the pair of first linkages 176b. In one optional implementation, a length of the pair of first linkages 176 is greater than a length of the pair of second linkages 196.

In addition, as shown in FIG. 8, in one optional implementation, the plurality of supports includes (i) a first support block 161 having a first end 162 coupled to the frame 156 and a second end 163 extending outwardly from the frame 156 and coupled to the prosthesis 120 below the first opening 130 and (ii) a second support block 161 having a first end 162 coupled to the frame 156 and a second end 163 extending outwardly from the frame 156 and coupled to the prosthesis 120 above the first opening 130.

In various embodiments, the second actuator 141 and the third actuator 142 may take the same form as the first actuator 140, as shown in FIGS. 3-8. In an alternative implementation, the second actuator 141 and the third actuator 142 may each include a plurality of cables coupled to and extending across a width of the second panel such that a first end of each of the plurality of cables is anchored to the wall 126 of the socket 125 and a second end of each of the plurality of cables extends through one or more channels in the wall 126 of the socket 125 to a ratcheted knob configured to manually wind or unwind the plurality of cables to retract or advance the second panel 136 in the second opening 131 and the third panel 137 in the third opening 132.

Figure 10:
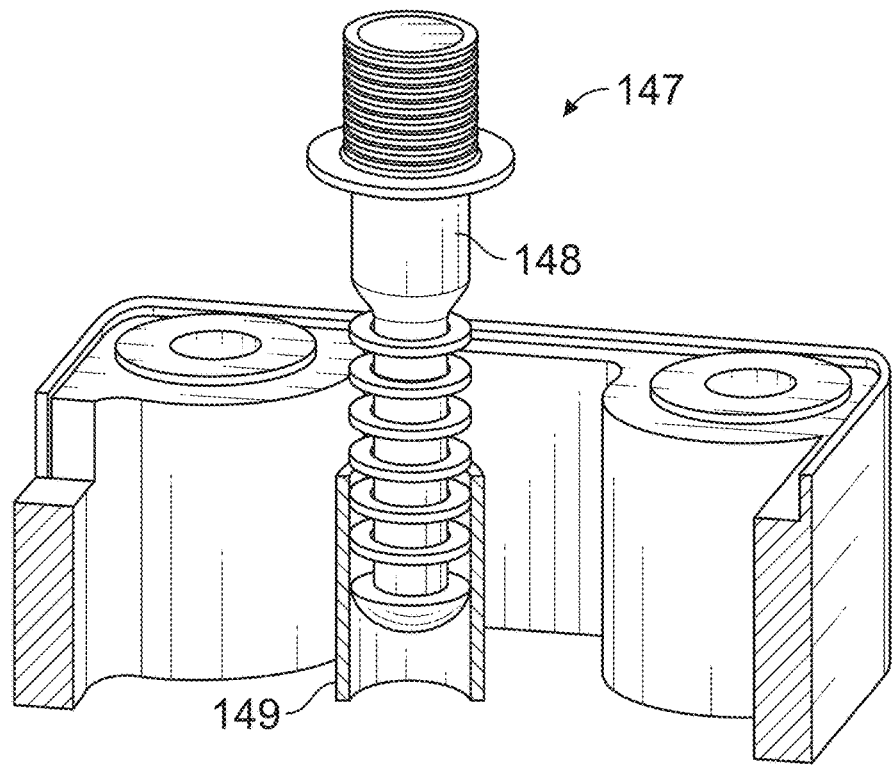
FIG. 10 is a side cross-sectional view of the pin sensor and housing according to one example implementation.

In one optional implementation, as shown in FIGS. 9-11, the apparatus 105 may further include a pin sensor 147 arranged at a bottom 124 of the socket 125 and configured to receive a locking pin 148 coupled to the liner 150 arranged over limb. The locking pin 148 is typically made of steel. In one optional implementation, the pin sensor 147 is an inductive sensor that includes coil windings on the exterior of a sleeve 149 that receives the locking pin 148. The coil windings are coupled to a capacitor and, optionally, a thermistor.

The pin sensor 147 is configured to obtain limb-depth data corresponding to a depth of the limb in the socket 125. As used herein, the "limb-depth data" includes information about the depth of a locking pin 148 in the pin sensor, as well as a corresponding time of detection. The processor is communicatively coupled to the pin sensor 147. The processor 202 is further configured (v) to receive the limb-depth data from the pin sensor 147 and (vi) to determine the socket-size adjustment further based on the limb-depth data. In another implementation, the processor 202 is further configured (vii) to determine that a current operating mode is one of a walking mode, a low activity mode and a rest mode based on the limb-to-socket gap data and the limb-depth data and (viii) to determine the socket-size adjustment further based on the current operating mode.

IV. Example Methods

Referring now to FIG. 11, a method 300 is illustrated for automatically adjusting a socket size of a prosthesis 120 using the apparatus 105 of FIGS. 1-10. Method 300 includes, at block 305, a processor 202 receiving the limb-to-socket gap data from the first sensor 145. Then, at block 310, the processor 202 determines a socket-size adjustment based on the limb-to-socket gap data from the first sensor and the predetermined socket-fit value. Next, at block 315, the processor 202 generates the command with the socket-size adjustment. And, at block 320, the processor 202 sends the command with the socket-size adjustment to the first actuator 140 to advance or retract the first panel 135 through the first opening 130. In operation, the processor 202 continuously receives limb-to-socket gap data based on a set time step and iteratively determines a socket-size adjustment to thereby effect automatic adjustment of the socket size. The time step may vary based on the current operating mode. For example, data will be obtained from the sensors 145, 146 as often as is required to maintain a proper fit for the current operating mode, but will also be minimized to the extent possible in order to conserve power.

The sampling rate (i.e., time spent obtaining data) is a separate consideration from the time step used to determine when to power on the various sensors to obtain relevant data. In one non-limiting example, sampling at a rate of 32 Hz is necessary in order to capture an entire step corresponding to a user's walking action. The sampling rate would increase for an activity like running and decrease for an activity like standing. These steps may be repeated in an ongoing and continuous manner as the limb-to-socket gap data is continuously obtained by the first sensor in a stepwise manner. And the actuator responsively and automatically adjusts the socket size of the prosthesis based on the commands received from the processor 202.

In one optional implementation, the apparatus 105 further includes a second sensor 146 coupled to the wall 126 of the socket 125. And the processor 202 is communicatively coupled to the second sensor 146. In this implementation, the processor 202 further receives limb-to-socket data from the second sensor 146. Then, the processor 202 determines the socket-size adjustment further based on the limb-to-socket gap data from the second sensor 146. In one non-limiting example, a mean value may be calculated by the processor 202 for the limb-to-socket gap data obtained from the first sensor 145 and the second sensor 146.

In one optional implementation, the apparatus 105 further includes a pin sensor 147 arranged at a bottom 124 of the socket 125 and configured to receive a locking pin 148 coupled to a liner 150 arranged over the limb. The pin sensor 147 is configured to obtain limb-depth data corresponding to a depth of the limb in the socket 125. And the processor 202 is communicatively coupled to the pin sensor 147. In this implementation, method 300 further includes the processor 202 receiving the limb-depth data from the pin sensor 147. And the processor 202 determines the socket-size adjustment further based on the limb-depth data.

In yet another implementation, method 300 includes the processor 202 determining that a current operating mode is one of a walking mode, a high activity mode, a low activity mode and a rest mode based on the limb-to-socket gap data and the limb-depth data. Other modes are contemplated, including, but not limited to, a jogging mode, an uphill walking mode, a stair-climbing mode, a sports mode for a particular sport associated with quantifiable sensor detection. As used herein, "modes" refers to states that have quantifiable regular activity that has the same control system features or settings. And the processor 202 determines the socket-size adjustment further based on the current operating mode. The apparatus 105 may include a third sensor in a distal anterior location in the wall 126 of the socket 125 to obtain data for the processor 202 to determine a current operating mode is a walking mode, as one optional implementation.

Figure 12:
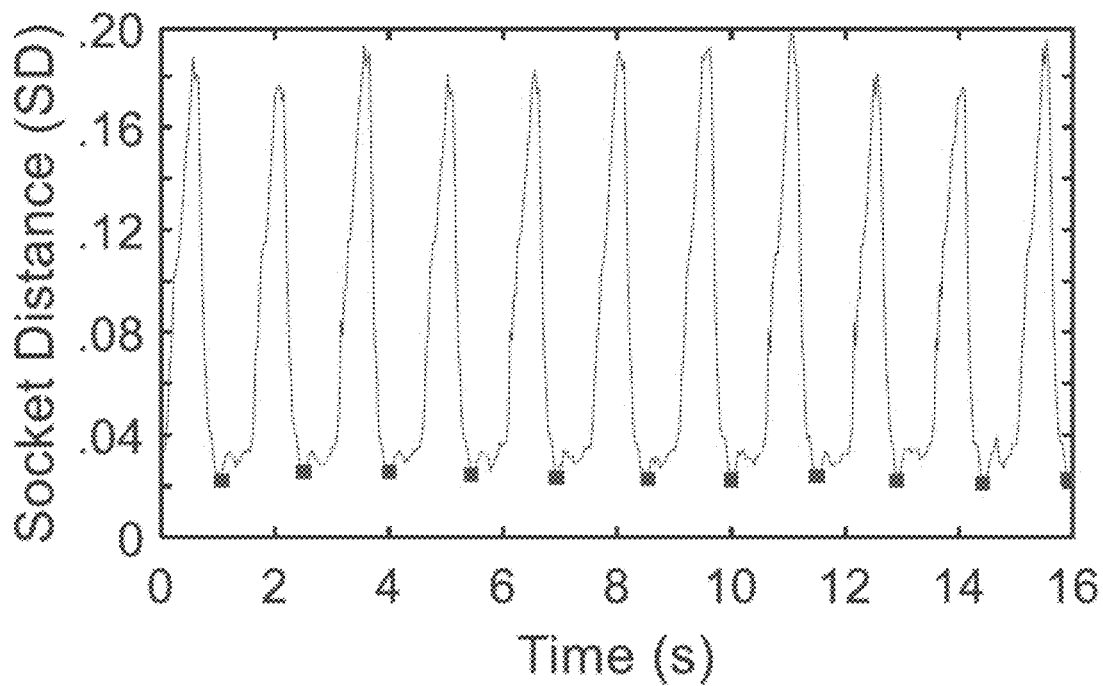
FIG. 12 is a graph showing the change in sensed distance between the socket wall and the limb over time.

In one implementation, the processor 202 determining that the current operating mode is the walking mode includes the processor 202 identifying the five most recent peak-to-peak amplitudes for the five most recent local minima and five most recent local maxima for the distance between the limb and the wall 126 of the socket 125 based on the limb-to-socket gap data, see FIG. 12 as one example and the discussion in Example 1 in Section V below. Then, the processor 202 determines that none of the five most recent peak-to-peak amplitudes is more than 25% greater than an average value of the five most recent peak-to-peak amplitudes and that none of the five most recent peak-to-peak amplitudes is more than 25% less than the average value of the five most recent peak-to-peak amplitudes. And the processor 202 determines that a cadence time between each of the successive local minima of the at least five most recent local minima is less than a cadence threshold based on the limb-to-socket gap data. In other words, "cadence time" refers to the period between each local minimum. In one optional implementation, the cadence threshold is 5.1 seconds. Alternatively, the cadence threshold may range from 1 second to 30 seconds, including but not limited to a cadence threshold of 1 s, 2 s, 5 s, 10 s, or 30 s. A shorter threshold period increases potential instability of the processor's performance (i.e. determined socket-fit adjustments), whereas a larger threshold period permits a more consistent pattern to be observed by the processor and thereby decreases the risk that the processor's performance will lead to instability.

In another implementation, the apparatus 105 further includes a pin sensor 147 arranged at a bottom 124 of the socket 125 and configured to receive a locking pin 148 coupled to a liner 150 arranged over the limb. The pin sensor 147 is configured to obtain limb-depth data corresponding to a depth of the limb in the socket 125. And the processor 202 is communicatively coupled to the pin sensor 147. In this implementation, the processor 202 determining that the current operating mode is the low activity mode includes the processor 202 determining that a most recent pin height minimum is below a pin height threshold based on the limb-depth data. Here, the pin height threshold is determined by the processor based on pin height minima detected by the pin sensor over a preceding predetermined period of time. For example, a user's limb has been observed to move to a deeper position in the socket 125 of the prosthesis 120 after a period of low activity. As such, the preceding predetermined period of time may correspond to a typical period of low activity that generally precedes a lower pin height minimum or increased pin depth.

In one example implementation, method 300 may include determining the current operating mode is the rest mode, based on data obtained by the third sensor in the distal anterior location in the wall 126 of the socket 125 and/or on data obtained by the pin sensor 147. For example, the processor may determine whether the signal from the third sensor and the pin sensor 147 is changing and to determine whether the liner on the limb has tighter fit with the wall 126 of the socket 125 to identify a rest mode.

In one implementation, method 300 includes, in response to a determination that the current operating mode is the rest mode, the processor 202 determining that the socket-size adjustment is 1% of the predetermined socket-fit value. In operation, in the rest mode, a panel release for socket expansion will involve smaller distances relative to those in walk and low activity modes to avoid a situation in which a user forgets or does not appreciate that socket release was conducted and attempts to rise and walk before a retention adjustment reducing socket size is achieved. In the rest mode, the total number of socket-size adjustments in combination would not exceed 1% of the socket volume that was achieved immediately before entering the rest mode. This reduces the risk of a user rising up and then falling due to a socket volume being oversized. In one implementation, a user could override this limitation and manually control the socket size via feedback provided from a remote computing device 216. In the walking mode, the socket-size adjustments may range from 0.2% to about 0.4% of socket volume. That said, there may be multiple socket-size adjustments implemented throughout an ongoing period of walking that may ultimately add up to more than a 1% volume change.

In one implementation, method 300 includes the processor 202 receiving the predetermined socket-fit value from a user. A user may submit this information to the processor 202 via a remote computing device, such as a tablet 216a, a personal computer 216b, a laptop computer 216c and a mobile computing device 216d. The range of socket-size adjustments can be set by a prosthetist when fitting a user. As one non-limiting example, a prosthetist may determine that a user should not exceed a +/−2% change in the predetermined socket-fit value (SFM) when the panels are in a flush neutral position with the wall 126 of the socket 125 in order to improve user safety. This restriction can be programmed into the processor such that the user cannot alter the setting.

As discussed above, a non-transitory computer-readable medium having stored thereon program instructions that upon execution by a processor 202 may be utilized to cause performance of any of functions of the foregoing methods.

As one example, a non-transitory computer-readable medium having stored thereon program instructions that upon execution by a processor 202, cause performance of a set of acts includes receiving the limb-to-socket gap data from the first sensor. Then a socket-size adjustment is determined based on the limb-to-socket gap data from the first sensor and the predetermined socket-fit value. Next a command is generated with the socket-size adjustment. And the command is sent with the socket-size adjustment to the first actuator to advance or retract the first panel through the first opening.

V. Example 1

A system is presented for monitoring socket fit via tracking a distance measurement between a liner (sock) in a prosthesis and the rigid wall of the prosthesis. An embodiment of the system was fabricated and tested, and becomes an exemplary embodiment with which to explain the system disclosed herein.

Test Prostheses

Sockets: Sockets with motor-driven, three-panel, adjustable panels were constructed for study participants. Panels were located anterior medial, anterior lateral, and along the posterior midline, similar to positions commonly used in RevoFit™ sockets. The participants' regular socket shape was duplicated by scanning their normal socket using an industrial coordinate measurement machine (FARO Platinum Arm, Faro Technologies, Lake Mary, FL). Sockets were fabricated with inductive sensors embedded within the socket wall to measure socket-to-target distance, termed "Sensed Distance" (SD) in this study. The sensed distance was taken to be representative of the limb-to-socket distance. The cable that ran through the three panels was connected to a motor within a housing (505 g) positioned immediately beneath the socket. As the motor drew in cable, the panels displaced radially inward. When the motor released cable, the panels displaced radially outward. The motor was controlled using a single-board computer (LattePanda, Shanghai, China) with an integrated microcontroller (Arduino Due) and a custom shield to execute motor control. The computer, microcontroller, and motor-control board were housed within a custom enclosure (total weight 648 g) mounted in a waist belt. TightVNC software (GlavSoft, Tomsk, Russia) was added for remotely connecting to the device. All data was logged by a controller operating in LabVIEW (NI 2017, National Instruments, Austin, TX) running on the single-board computer. Since all data was logged locally, once the device was started it did not require a remote connection to control the motor.

Liners:

Iron powder incorporated into the participant's prosthetic liner served as a magnetic target for the inductive sensors. The liner was purchased for research purposes from a commercial liner manufacturer (Willow Wood, Mt. Sterling, OH). The iron concentration in the liner was approximately 80% by weight, similar to a ferrous sheath developed previously, and it was contained within the outer 1 mm of the elastomer. As with most prosthetic liner products, there was a fabric backing over the outside of the elastomer, thus the fabric backing and adhesive holding it in place were between the magnetic target and the sensor. The fabric backing and adhesive were an elastic element of approximately 1.3 mm thickness. The inductive sensor measured distance across this elastic element when the liner was in contact with the socket, and distance through air and the undeformed elastic element when it was not. The liner and sensor were calibrated using an inflatable bladder positioned within the socket. Bench testing of the sensor-liner system demonstrated errors of less than 2.8% full-scale. A certified prosthetist fit the test prostheses to study participants and helped them select an appropriate sock thickness such that the socket was comfortable at the neutral panel position (flush with socket). Participants did not wear socks when using the test prosthesis.

Socket Fit Metric

One aspect of the automatic socket control system is the definition of the Socket Fit Metric (SFM), derived from continuous SD data. Six SD sensors were located on the socket, positioned at proximal, mid-limb, and distal locations. Past studies have shown that the stance minimum within each step, when the SD is fully loaded, is a favorable indicator of socket fit during walking. During pilot testing, a survey of the six sensors showed that the posterior medial mid-limb SD (location shown in FIG. 9) was the best combination of lowest error and highest signal from changes in socket size. A typical human subject time series corresponding to several steps from a posterior medial mid-limb SD sensor was plotted with sensed distance SD vs. Time in FIG. 12. A small SD value indicates a small distance between the socket and the liner. The stance and swing phases of the step were easily identified. The stance minima for each step are also indicated. Because the socket fit control method is computed on a fixed time step, the value of the SFM is assumed constant between steps (i.e. a zero-order hold).

Figure 13:
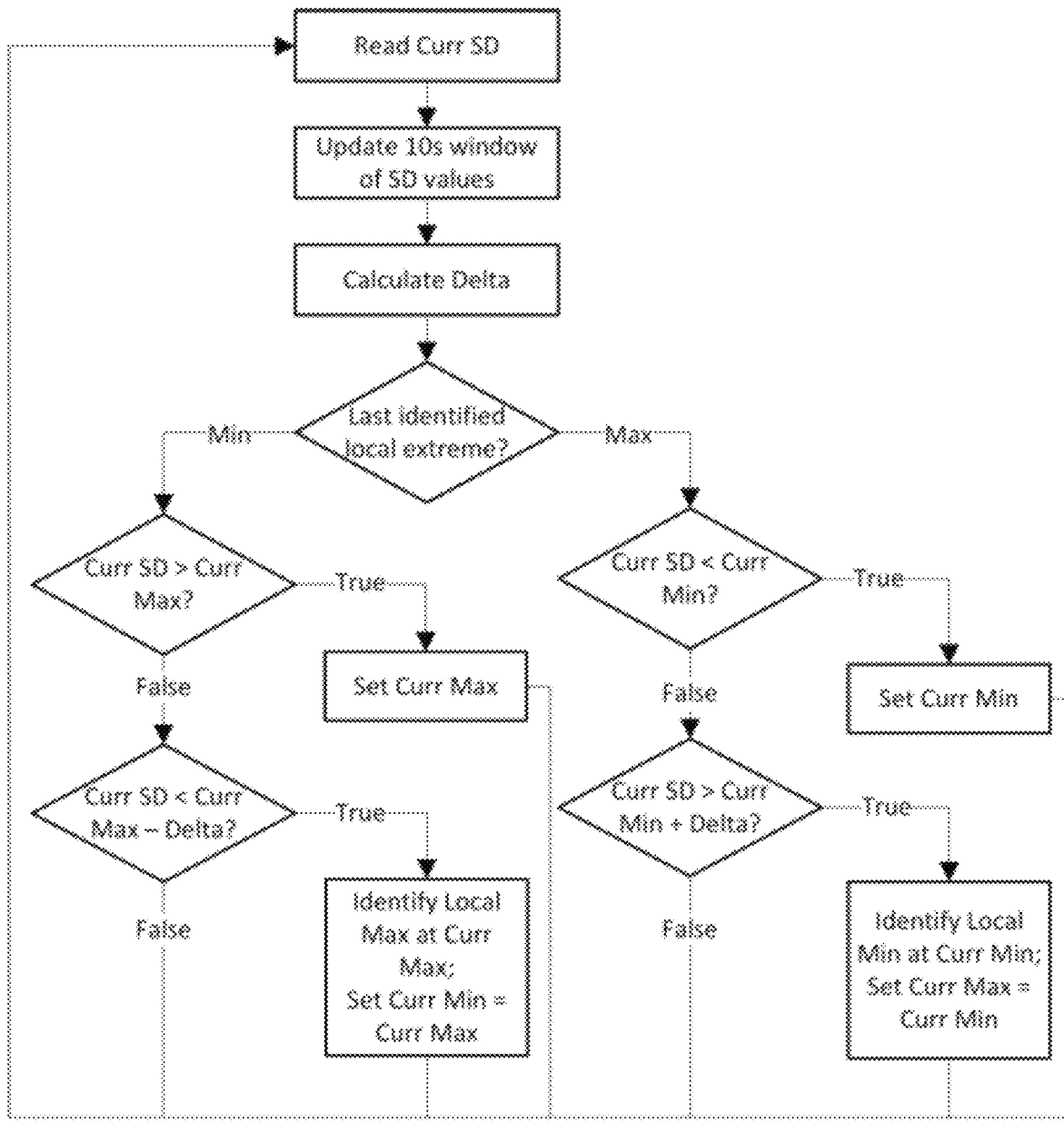
FIG. 13 is a flow chart according to one example implementation of the control system.

As shown in the flow chart for FIG. 13, local minima and maxima for SD were determined. The Delta value shown therein is equal to the average of the minimum and maximum socket distance SD within a 10 second moving window. And the SFM is the moving average of the SD value at the last five identified local minima detected.

Controller

A method for automatically controlling the size of the socket to compensate, during walking, for the unknown changes in limb fluid volume was developed. The controller continuously measures socket "fit" and adjusts the socket geometry to maintain a prescribed reference set point.

Figure 14:
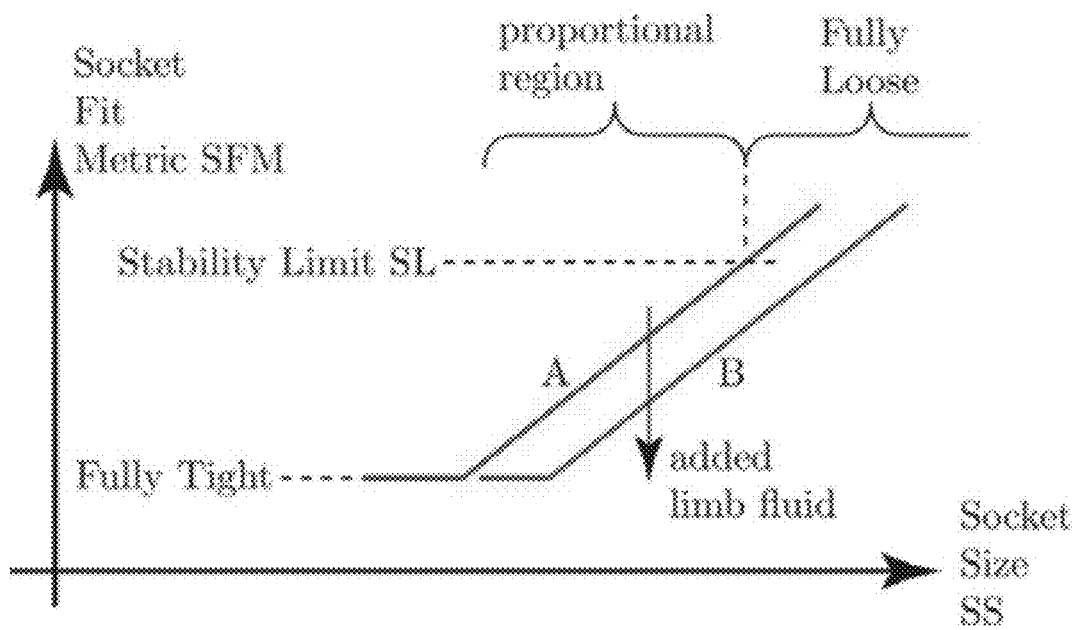
FIG. 14 is a graph showing the relationship between Socket Fit Metric (SFM) and Socket Size (SS)

Consider first the static (steady-state) characteristics of the limb-socket system. FIG. 14 shows the relationship between the SFM and socket size (SS). The SFM, inferred from the SD sensors, is a measure of the looseness of the fit between the socket and residual limb: a small SFM indicates a tight fit and a large SFM indicates a loose fit. Socket Size is a measure of the effective volume of the socket, as determined from motor encoder data. Curve A in FIG. 14 shows that when SS is very small, the socket is fully tight, and the SFM is approximately constant. Further, lowering of SS merely forces fluid from the limb, with no corresponding change in SFM. As SS is increased, for a constant limb fluid volume, the system enters an approximately proportional region in which the SFM increases monotonically. Eventually, the stability limit (SL) is reached as socket size increases, where the socket becomes too loose for comfortable (or safe) use. If, while holding SS constant, additional fluid is added to the limb, the curve-A is forced downward to curve-B, for example. The constant of proportionality and the fully tight limit remain the same. On this new curve-B, SS must be increased to reach the stability limit.

The goal of automatic prosthesis control during walking is to maintain the SFM at a level just below the stability limit. This will maximize limb fluid volume, while ensuring stable operation. As limb fluid volume varies (i.e., gain or loss), the control system will adjust to sustain the operating point near the stability limit.

Figure 15:
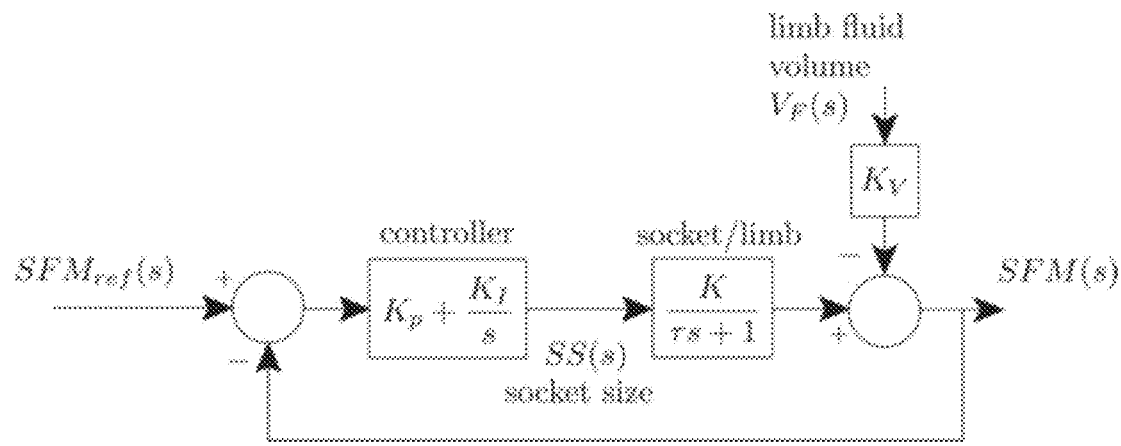
FIG. 15 is a schematic showing the automated socket fit control loop.

The control loop relating the socket fit set point (SFMref) to measured SFM is shown in FIG. 15. The socket/limb block relates the SS to the SFM. Changes in the SFM caused by changes in limb fluid volume are considered to be exogenous disturbances to be rejected by the controller. Open-loop experiments have shown that a first-order linear model of the socket/limb system is adequate for design purposes. For each participant, the model parameters, gain K and time constant τ, are identified from open-loop ramp and step responses, respectively. Note that K is the effective slope of the proportional region in FIG. 14.

The controller determines the mechanical changes in SS implemented through the motor/winch mechanism. The parameters (KP and KI) of the proportional-integral (PI) controller are selected to produce a critically damped second order closed loop system, with response time only moderately faster (0.8 τ) than the open-loop system. Thus derived, the system has zero steady-state error for a step change in the set point SFMref, and zero steady-state error for a finite increase in limb fluid volume.

Figure 16:
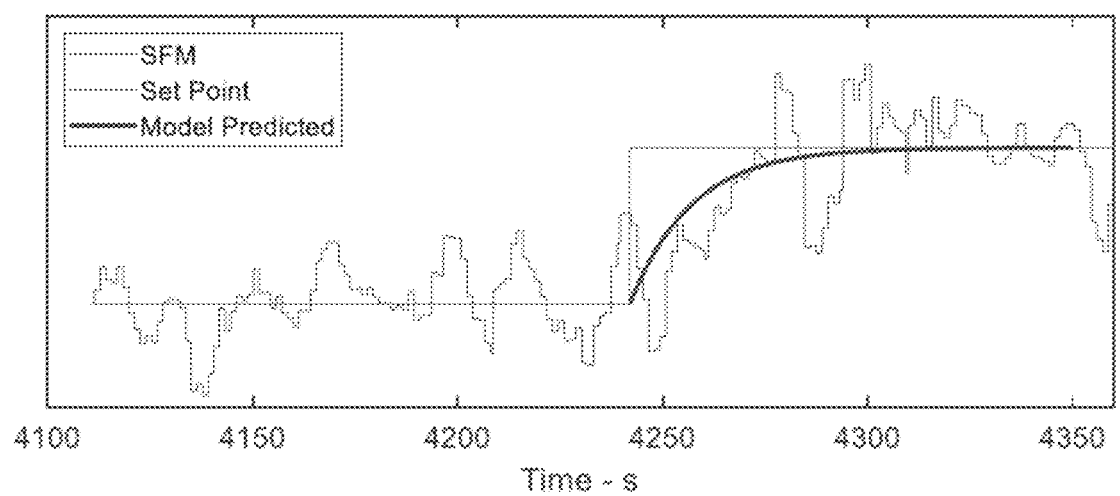
FIG. 16 shows recorded SFM and system set point over time along with a predicted model response overlaid.

The nominal performance of the SFM controller is shown in FIG. 16. After the participant had been walking for several minutes, a step change in the SFM set point was commanded. The amplitude of the step is small in comparison to the proportional range described in FIG. 14. The system responds by increasing SS until the SFM settles at the new set point. Also shown is the model predicted response derived from the model of FIG. 15.

A walking detector was implemented to ensure the controller only operated during steady walking. Walking was considered detected when a threshold peak-to-peak amplitude during 5 continuous steps was detected, and walking cadence (period between local minima) was less than 5.1 s. Use of the walking detector ensured the SFM was in the proportional region of the SFM vs. SS diagram (FIG. 14), the participant's gait was not erratic, and weight-shifting during standing was not interpreted as walking.

For purposes of this study, the socket fit controller was implemented in LabVIEW, executed either on a desktop or single-board computer. Commands were sent from LabVIEW to a socket-mounted Arduino Due and shield that controlled the motor/winch mechanism. The Due sent motor position data to a previously described device, where it was packaged with SD data and sent to LabVIEW via a second serial connection. The sample rate of the socket control system was 32 Hz, the highest rate possible when querying the distance sensors sequentially to prevent interference.

Study Protocol

Each participant walked on the treadmill, wearing a harness for safety, while the controller was operated and sensor data (SFM) and cable length (socket size) were recorded. To quantify the controller's ability to maintain the set point, two tests were conducted: (1) Constant Set Point Test; (2) Adjusted Set Point Test. In the Constant Set Point Test, multiple walks, each at least 4 minutes in duration, were conducted. The set point for each walk was calculated from posterior mid-limb SD collected (open-loop) during the first 10 steps, and then the mean used as the set point value. The set point was maintained for the rest of the walk. Differences between SFM and set point data were calculated as described below. Between successive walks, participants stood for 1 minute, sat for 2 minutes, then stood for 1 minute before walking again. In the Adjusted Set Point Test, which was completed if participants were not fatigued after the Constant Set Point Test and willing to conduct more trials walking on the treadmill, participants walked with automatic control continuously engaged at least 1 minute. During the walks, the researcher adjusted the set point up or down by 1000 sensor count, the equivalent of an SD change of about 0.008 mm, and the SFM response was observed. Differences between SFM and set point data were calculated. Session duration was approximately 34 minutes.

Analysis

For both the Constant Set Point Test and the Adjusted Set Point Test, the operational effectiveness of the proposed automatic socket control was judged by its ability to maintain the SFM set point. Typically, the measured SFM and its set point are plotted as functions of time. In addition, the control error, summarized for each walk as the average Integral Absolute Error (IAE), was estimated as:

$$\overline{IAE} = \frac{1}{N} \sum_{i=0}^{N} |SFM_0 - SFM_i|$$

where $SFM_0$ is the SFM set point, $SFM_i$ is the measured SFM of the ith temporal index, and N is the number of data points in the walk. IAE distribution was characterized across the test participants by making a histogram of IAE for 0.001 mm bins of error.

For the walks where the set point was adjusted during the walk, the Adjusted Set Point Test, IAE was plotted against time to visualize how quickly IAE stabilized after a new set point was specified.

Results

Ten people with trans-tibial limb amputation participated in this study, 9 males and 1 female. All participants had their amputation as a result of traumatic injury. Median participant age was 51 years (range 26 to 75), and median time since amputation was 29 years (range 4 to 49). Median residual limb length was 16.2 cm (range 11.5 to 21.8), and median mid-limb circumference was 29.6 cm (range 26.2 to 36.5). Median socket volume below the patellar tendon was 1377 mL (range 1184 to 2591). The median length and width of an anterior panel (medial or lateral) was 9.3 cm and 4.1 cm with ranges of 6.3 cm to 15.5 cm and 2.9 cm to 6.0 cm, respectively. The median length and width of a posterior panel was 8.6 cm and 5.1 cm with ranges of 6.7 cm to 13.0 cm and 3.9 cm to 6.1 cm, respectively.

Figure 17:
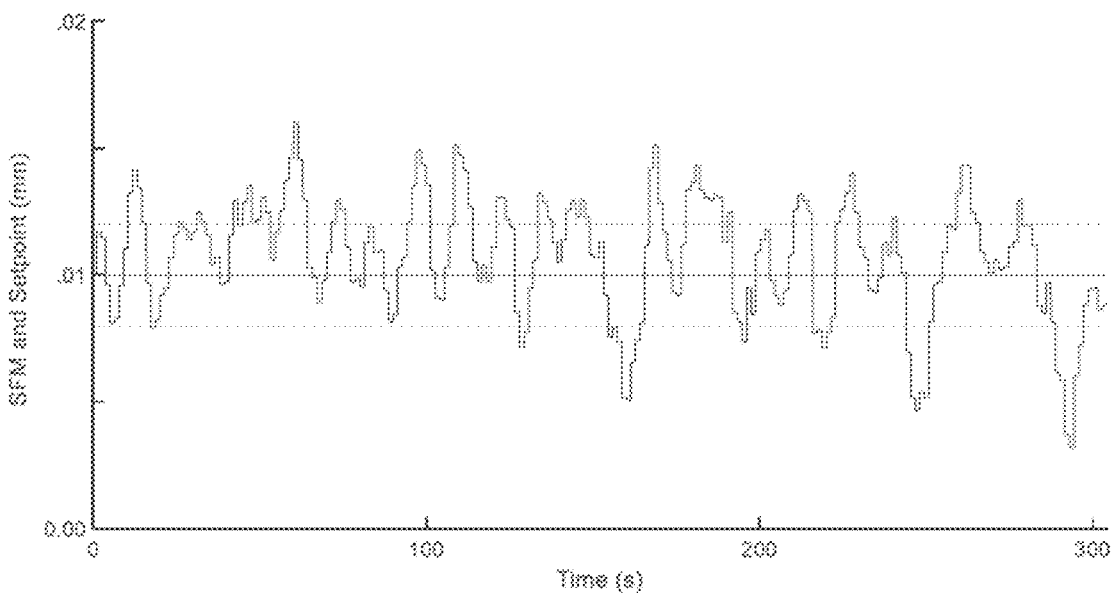
FIG. 17 shows the control system's reading of SFM versus a single set point over time.

Segment duration, where a segment refers to walking under continuous control, ranged from 78 s to 924 s. IAE normalized to the number of points for all walking segments ranged from 0.001 to 0.046 mm with a median of 0.003 mm. An example SFM v. time plot with IAE as dashed lines is shown in FIG. 17.

Figure 18:
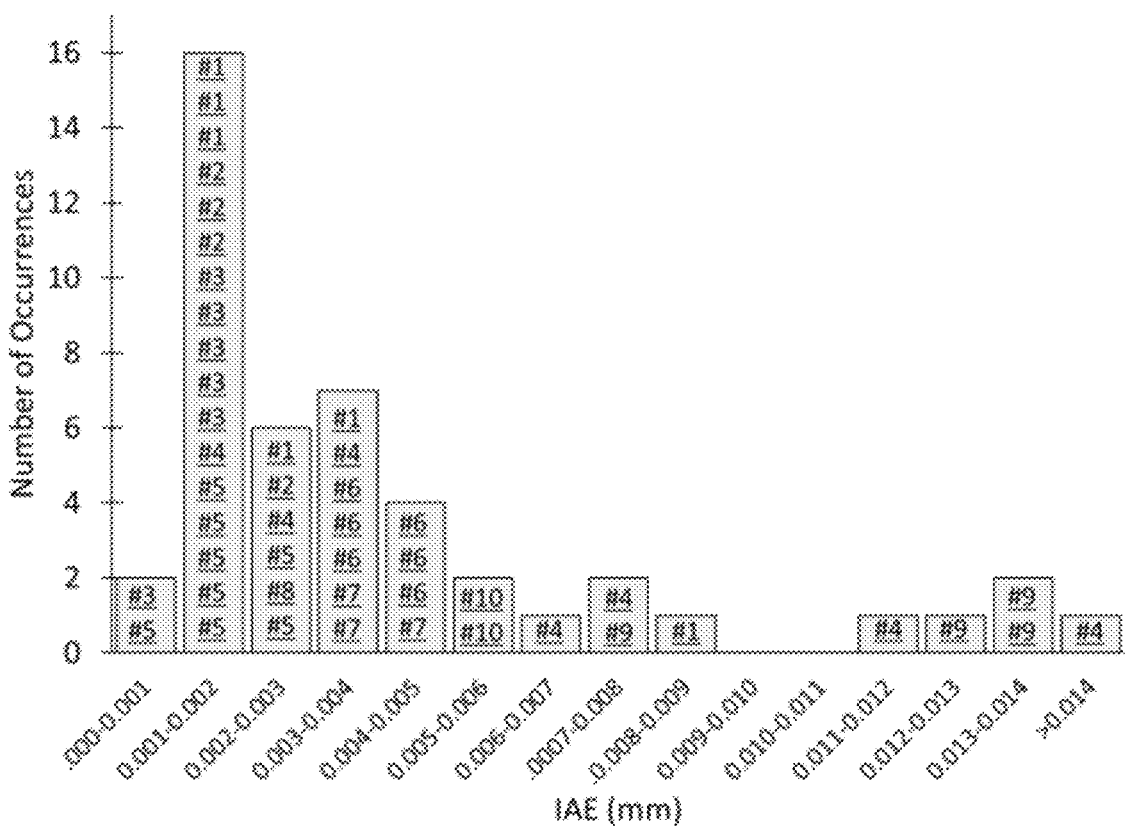
FIG. 18 shows the distribution of measured Integrated Absolute Error (IAE) in mm for segments of walking activity for different participants.

A histogram of IAE showed that 80% of the walks had IAE values less than 0.006 mm (FIG. 18). Walks with errors larger than 0.010 mm were from two participants #4 and #9. Analysis of motor position v. time data revealed that some participants, including participants #2, 4, 5, 7, and 9, had their socket larger than neutral (flush panels) part of the time during their first test.

Figure 19:
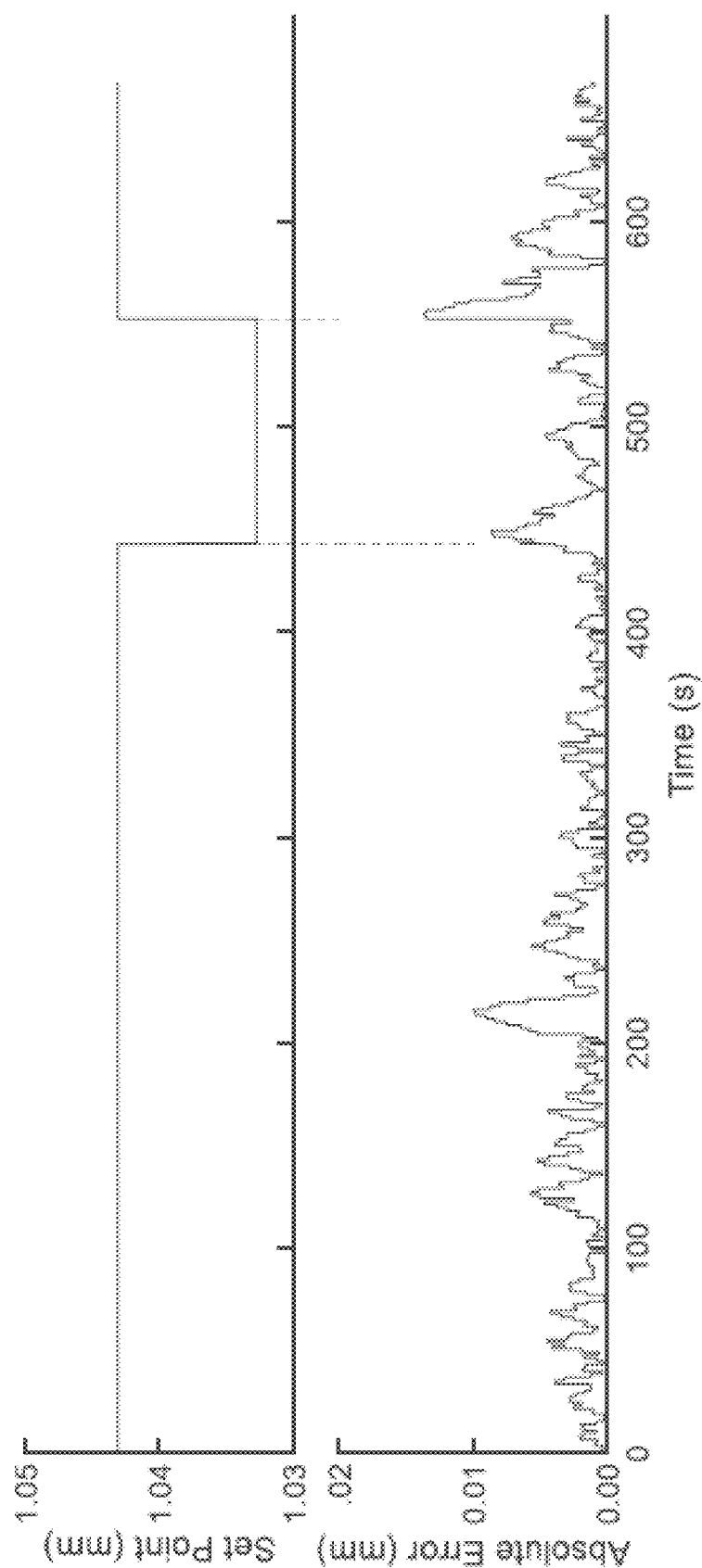
FIG. 19 shows an example demonstrating control system absolute error during an Adjusted Set Point test.

Six participants conducted the Adjusted Set Point Test— #1, 3, 4, 5, 6, and 8. IAEs for all participants ranged from 0.001 mm to 0.005 mm (median 0.003 mm). An example plot of absolute error vs. time is shown in FIG. 19. As shown in this example, error increased immediately upon a socket size change and then subsequently returned to normal baseline values.

Adjustable sockets under automated control have the potential to improve comfort and usability of prostheses for people with limb amputation. By maintaining fit, sockets under automated control relieve prosthesis users of the distraction of continually monitoring and adjusting their socket. In this control system, a socket fit metric based on socket distance data was implemented.

In this study, an active control system was shown to effectively maintain a set point based on a measured-fit metric, while a person with limb amputation ambulated wearing an adjustable-size socket. Potentially, the control model and sensing element developed here are applicable to other adjustable socket technologies, for example a socket made using three flexible struts that surround a custom flexible liner. Socket size is adjusted using a cable around the outside of the struts (Infinite Socket™). A more recent design is a socket that wraps around a limb with an overlapping edge that is adjusted via ski-boot buckles extending across the overlap (IFIT™) [21]. Systems with electronic-driven actuators adjusted using a mechanical pump, which are more directly matched to the control system developed here, include elevated vacuum sockets (LimbLogic™, Harmony™ ePulse, VASS™), air filled bladders, and liquid filled bladders or tubes within the socket or liner.

To put the IAE results from this study in a clinically meaningful perspective, data was used from a recent study on a group of people with trans-tibial amputation investigating sensed distance changes across participants' range of tolerated socket volume. A 0.003 mm sensed distance error, the median IAE in the present study, corresponded to a median socket volume error of 0.08%. A single step adjustment using the motor-driven adjustable socket system, which was deemed a reasonable step size for all participants in the study, corresponded to a socket volume change between 0.27% and 0.36%. Thus, the IAE measured in the present study introduced a socket volume error of about ¼ of the volume change induced by a single motor step adjustment. This error is expected clinically acceptable.

The most meaningful source of IAE in this study was the single cable design of the adjustable panel system. A single cable connected all three panels to each other. At a given cable length, individual panels may have "floated" relative to the socket, taking on different radial positions at different times during testing. Using a socket with panels individually controlled, for example a socket with one motor per panel, would overcome this problem and potentially improve control system performance.

VI. Example 2

A panel-pull system was designed with one mechanism spanning across each of three panels. The side supports (aluminum 7075) were made in three differing lengths to accommodate various panel heights. These units spanned 10.2 cm (short), 12.7 cm (medium), and 19.1 cm (long) distances. Custom side supports were connected to bearing blocks that directly mounted to the socket. These blocks were covered so that the resin did not fill the threaded holes. The covers were removed after the lamination was complete. The lead screws were ¼-16 ACME thread of opposing directions connected by a rigid coupler in the center and bearings on opposing sides. A motor (1717T006SRIEH2-4096+15A 152:1+MG03, Micromo, Clearwater, Florida) drove gearing that connected to the end of a lead screw which translated the motor's rotation to axial movement of the travel nut. The travel nut had connection points for arm linkages. These arm linkages were mounted to the socket panel via a mount that was laminated into the panel during fabrication using a positioning jig to ensure proper alignment and translated the axial movement of the travel nut to a perpendicular linear movement of the panel. This perpendicular linear movement equated to the radial displacement of the panel. By changing the direction of the motor rotation, the radial direction (tightening or loosening) of the panel was changed. In FIG. 8, the arrows show inward and outward panel movement.

Strapping was adhered to the liner fabric by heat activated fusing web. The strapping was threaded through cutouts in the panel where they were tied off.

The motors on the panels were controlled using a virtual instrument (VI) (LabView, National Instruments, Austin, Texas) connected to the socket via a 25-cm cable. The researcher used the VI to select panel position in mm relative to neutral (flush) according to the study protocol described below. All three panels were moved the same distance simultaneously. The VI sent commands (motor position) to a microcontroller (LPC54114x, NXP, Eindhoven, Netherlands) on an electronics board mounted on the ankle of the prosthesis. The microcontroller relayed those commands in the form of pulse width modulation (PWM) to a motor driver (DRV8835, Texas Instruments, Dallas, Texas) which drove the three motors (6V, Micromo) all at the same duty cycle. The encoders on the motors provided feedback to the microcontroller. Those signals were decoded using a quadrature counter (LS7366R, LSI/CSI, Melville, New York) with an SPI interface. The microcontroller maintained the panel position communicated by the VI within 0.02 mm for positions tighter than flush and 0.08 mm for positions looser than flush.

The motor encoder recorded the motor's rotation in degrees. The gear ratio from motor to shaft was 2:1. Thus, one full rotation of the motor (360°) resulted in the shaft rotating 180° and the travel nut moving ⅟₃₂" (0.79375 mm) along the shaft. The linkage from the travel nut to the panel was 35.56 mm. This movement along the shaft (variable x) resulted in panel displacement (variable y) perpendicular to the shaft as given by the equation: $y=\sqrt{35.56mm^2-x^2}$. Thus, radial change in mm were directly related to encoder counts in degrees by substituting x=degrees*0.002205 mm/° into the above equation. The panel flush position of the system was 24.78 mm x and 25.50 mm y because the shaft was 25.50 mm from the surface of the panel when mounted. The system allowed for approximately 10 mm radial movement out and 5 mm radial movement in from the flush position. The actual range of the system was from 18.28 mm to 32.00 mm in the x direction corresponding to radial panel displacements of 30.50 mm (tightest possible) and 15.50 mm (loosest socket possible), respectively.

VII. Example 3

Contrary to traditional belief, many prosthesis users, particularly those without peripheral arterial disease, gain limb fluid volume during walking. This is thought to happen because of the increased heart rate and arterial pressure that occur when a person transitions from standing to walking. With the added vascular drive, more extracellular fluid is driven across the arterial walls into the interstitial space within the residual limb without a corresponding increase in interstitial to venous transport and fluid volume movement out of the limb. The result is an increase in limb volume. Releasing socket pressures during sitting after walking is a second opportunistic way to facilitate limb fluid volume recovery for people who lose volume earlier in the day. Studies have shown that socket releases of 10 or more minutes are sufficient to recover and retain fluid volume during subsequent ambulation. Frequent socket releases of shorter duration (<10 minutes) may also be effective, including durations less than 3 minutes.

One goal is to reduce weight of the auto-adjusting socket closer to that of a traditional prosthesis, which may improve usability and clinical acceptance. From experience, some participants do not like prostheses heavier than their traditional prosthesis. Implementing the auto-adjusting socket on the posterior panel only would allow us weight reduction of the socket by about 320 g. To initiate this effort, the auto-adjustment system was operated with posterior panel adjustment only (the two anterior panels were kept stationary) on two participants. Test results showed that the match between SFM data and the set point was comparable to that of the three-panel system.

Testing of the 3-panel auto-adjustment system in outdoor tests with variable duration walking, standing, and sitting demonstrated performance comparable to treadmill tests during times participants were walking, but there were occasional difficulties at the start of a new walk after prolonged low activity or sitting. This may be due to the limb shifting or reshaping in the socket, the SFM was too far from the set point at the outset of walking, and/or the SFM changed rapidly during the early part of the walking bout. The auto-adjustment method for the walking function did not respond well to these conditions. These results provide impetus for low activity and sitting functions to be incorporated into the auto-adjusting socket to manage socket fit during low activity and sitting.

To rectify this problem in the short-term so that take-home testing could be conducted, three changes were made to the auto-adjustment method for walking. First, a "soft lock" set point was implemented, whereby at the outset of a new walk if the current SFM was more than 1× the Plant Gain away from the current set point then the set point was adjusted to the current SFM. Plant Gain is the slope of the SFM v. socket size. This essentially "resets" auto-adjustment to the new socket fit. If the current set point was less than 1× the Plant Gain, then the auto-adjustment operated as normal. Second, a ±2.00 mm range limit was placed around the set point so as to limit the method from conducting large rapid socket size changes early in a walking bout. Third, a mobile phone app was modified so that the user could manually adjust the set point (tighter or looser) if desired. Thus, users could not change the socket size, but they could change the set point.

An infinite impulse response (IIR) filter was also implemented to manage integral error buildup when intermittent walking with frequent short breaks of weight-shifting was conducted. Results from testing the new auto-adjustment system showed improved performance.

Take home tests for 3 days were conducted on three participants during development of the auto-adjusting socket. The auto-adjustment algorithm was activated each day, but not as often as expected. Though participants were active, they did not often walk continuously. Instead they were at work moving about within a building—standing, weight-shifting, or walking only a few steps at a time—not long enough to trigger the walk detection algorithm and turn on the auto-adjustment system. A method to manage low activity, periods with intermittent standing and short walking bouts, is needed. This functionality will reduce transition problems to walking and eliminate for the need for range limits and the soft lock. Previous 6-hour investigations outside the lab investigating limb fluid volume change for traditional sockets demonstrated that participants typically lost fluid volume during low activity, and the losses were significantly greater than those during high activity. Auto-adjustment during weight-shifting should accommodate those losses and achieve a more consistent SFM.

Additional take-home tests on the same three participants were conducted with the socket in other configurations. In manual mode, participants adjusted the socket at will using the mobile phone app (no auto-adjustment). Results showed that participants adjusted socket size during sitting to execute socket release, but in general did so only during long rest periods of more than 20 minutes. There were, however, numerous other opportunities for socket release of shorter duration. Presumably, socket releases were not executed more often because participants were occupied and did not want to be bothered. In prior studies, socket releases longer than 10 minutes were found to have facilitated limb fluid volume recovery and retention, though results from an ongoing study in the lab suggest that durations as short as 3 minutes may be sufficient for some people.

An auto-adjustment method that eliminates the distraction of manually executing socket release and then returning the socket back to the original size before walking may help to better maintain limb fluid volume during the day and enhance socket fit management and limb health. A Sitting auto-adjustment method should execute limited distance panel release since the user, forgetting that socket release was conducted, may rise and start walking quickly before the actuator returns the socket to a smaller size. While limiting panel release distance may limit the amount of fluid volume recovery and retention, if auto-adjusting socket release is conducted frequently this may still improve socket fit management relative to no panel release.

Utilizing a control system with settings for walking, high activity, low activity and sitting or rest will result in better fitting sockets with less residual limb discomfort and pain, less distraction to the user to operate and thus an improved quality of life and a more stable limb volume that may improve residual limb health and patient long-term outcome.

The present disclosure challenges current clinical paradigms, seeking to shift away from the practice of enlarging or reducing socket size upon user sensation of discomfort to an early-action philosophy based on adjustment when a measurable change in fit has occurred but is not yet discernable to the user. Capitalizing on opportunities to increase socket size during periods of limb volume recovery (continuous walking; socket release during sitting right after walking) is a practice not normally executed by people wearing traditional sockets. This is an innovative way to stabilize daily limb volume and maintain socket fit.

Custom sensors to monitor limb-socket distance and limb depth in the socket are implemented in this disclosure. The distance sensor uses an inductive sensing modality to measure distance between a custom antenna positioned in the socket wall during fabrication and an elastomeric liner with a ferrous polymer target embedded in its outer layer. The ferrous polymer can be added to almost any liner by removing the fabric backing and replacing it with our ferrous layer. The ferrous polymer had tensile properties consistent with that of commercial elastomeric liners, but high compressive stress and thus minimal sensitivity to limb-socket pressure. An inductive sensing chip (LDC1614, Texas Instruments) is used to drive the antenna. The circuit acts as an LC tank oscillator. When the magnetically permeable target, the ferrous liner, is brought near the antenna, it reinforces the inductor and lowers the sensor's oscillation frequency in a distance-dependent manner. The frequency measured by the chip is a sensitive measure of distance between the target and antenna. Durability testing did not show a trend of decreased or increased sensitivity over time.

The pin sensor provides a very sensitive measure of pin depth into the shuttle lock (FIGS. 9-10). When people walk wearing their prosthesis, the pin sensor detects the very small vertical up and down motions of the pin (between shuttle lock clicks) within the inductive element. The inductive sensor is a 30-AWG wire wrapped around a 3D-printed coil former. A thermistor is placed next to the coil winding in case thermal compensation is needed. Calibration testing showed consistent performance before and after amputee participant testing.

Single-Panel Vs. Multi-Panel Auto-Adjusting Sockets

Test sockets duplicate in shape to participants' traditional sockets are fabricated. Each person's traditional socket is scanned using a commercial 3D scanner (FARO Platinum Arm, Faro Technologies), then from the scan a foam positive carved (C7, Provel). A series of three layups are implemented. A 4-ply Nyglass stockinette is applied to the positive and infused with resin. After the layers cure, thin flexible inductive sensors are placed at anterior distal, posterior medial mid-limb, and posterior lateral mid-limb locations. These locations are selected based on prior study results demonstrating that the two posterior locations served as effective feedback signals for auto-adjustment, and the anterior channel served as an effective activity detector. A 1-ply carbon fiber layer is applied, and then small rectangular mounts to support the frame for the adjustable panel are applied. An outer layup of 1-ply carbon fiber, 2-ply Nyglass, and 1-ply carbon fiber is added, infused with resin, and cured. Panel locations are strategically selected where practitioners typically add pads. These areas of the residual limb are known to be load tolerant. Panel size is maximized in order to produce meaningful socket volume change but at the same time will avoid the bony prominences at the anterior distal tibia, tibial crest, and fibular head that may be sensitive to compressive stress.

Small motors (1724A006SRIEH2-4096, Micromo) (37 g) mounted to the frame of each panel are used to adjust socket size. To improve efficiency, power switches are re-routed so as to enable/disable the motor encoders while leaving the other peripherals as is. This capability will allow power management to be improved so that the auto-adjusting socket can be used longer during field tests before re-charging is necessary. Firmware changes include the addition of event logging to stored data to identify in the data stream when the controller makes a change as opposed to the participant manually making an adjustment using the mobile phone.

Participants use the same test socket throughout the study. The socket is capable of operation in a single-panel or three-panel mode via changes to settings in the code embedded in the micro-controller. The single-panel mode may require a greater panel displacement range since the socket volume change per increment that it induces is about 40% of that of the three-panel mode system. The posterior panel is typically larger than the anterior panels.

Method to Adjust Socket Size During Low Level Activity

Almost all participants with transtibial limb loss who have been tested using bioimpedance analysis lose limb fluid volume during low activity, i.e. stands with brief bouts of walking. This is unlike during high activity (continuous walking) where they tend to gain fluid volume. As such, socket size reductions are the primary adjustment to address when the Low Activity auto-adjustment setting is operating. In this case, the auto-adjustment system reduces socket size when the participant's limb becomes unstable and starts to move deeper into the socket.

The socket sensors on the posterior mid-limb, though they well identify socket fit changes and limb fluid volume losses during walking that may be precursors to limb downward displacement, do not well identify limb downward motion during standing or weight-shifting. However, the pin sensor in the distal socket that provides a very sensitive measure of pin height in the shuttle lock may provide such information. Analysis of data from a take-home test on a participant using the adjustable socket in manual mode (auto-adjustment off) showed that a consistent pin depth was maintained during the stance phase of walking but a deeper position after 19 minutes of low activity. As such, the pin sensor may provide an effective control system signal to manage socket fit during Low Activity based on pin sensor-socket size relationships during standing and weight-shifting.

In one embodiment, where single-panel auto-adjustment is effective, the anterior panels may be manually adjustable using a short, lightweight ratcheted knob and cable or a related mechanism for each panel. This design will allow the anterior panels' motor and frame hardware to be eliminated, reducing socket weight.

The control system will be implemented in a portable LabView™ module to allow the control method to be easily modified and updated. Use of this module permits reprogramming of the control system architecture during research, but in real-world operation, the earlier-described microcontroller will be used. The control system will use the anterior distal socket sensor to determine if the person is in the Low Activity state. The Low Activity state is characterized by stands, weight-shifts, and short walks (a few steps at a time). The Low Activity SFM (socket fit metric) is determined from the pin sensor minima during each cycle. A cycle is defined as a local maximum to a local minimum to a local maximum, thus essentially a weight shift to and from the prosthetic limb. Unlike the Walking auto-adjustment method, the Low Activity method is not expected to need frequent socket size adjustment. Doing so may accentuate fluid volume loss. This has been observed anecdotally in the lab using bioimpedance analysis to monitor limb fluid volume. A method that uses a moving average of the pin sensor minima during weight shifting is used.

Method to Adjust Socket Size During Sitting

Socket release during sitting has been demonstrated to facilitate limb fluid volume recovery and retention during subsequent walking. The intent of the Sitting setting in the control system is to execute panel release during sitting in such a way that limb volume recovery is achieved but at the same time avoid sockets that are too loose and that may put participants at risk of a fall should they stand up before socket return to the pre-sit size is completed.

Small socket releases during rest of approximately 1% socket volume, approximately equivalent to removing a 1-ply sock, are contemplated to induce meaningful fluid volume recovery and retention. A 1% level is selected based on prior investigation where some participants found that walking with a 2% socket enlargement right after sitting was uncomfortable. The socket is released 1% during rest (i.e., sitting) and then returned back to its pre-rest size when the participant prepares to ambulate. If participants start to walk before the Sitting method completes, they will not be at high risk of a fall. One option is to repeatedly execute 1% socket releases over the day for this intervention to have a beneficial impact, given the anticipated small fluid volume recovery each time. In activity data collected on 21 participants with transtibial amputation in their free-living environments and other initial studies, participants were found to have rested for short durations frequently. As such, there may be opportunities for frequent socket releases during the day for many prosthesis users.

The Sitting auto-adjustment method is implemented using data from the anterior distal socket sensor and the pin sensor. When sitting is detected, where there is a high anterior distal sensed distance and a high pin position within the shuttle lock, the panel will be released to accomplish at least a 1% socket volume change. However, in systems that are programmed to reduce socket size upon detection of movement, then the socket size release may be up to a 5% socket volume change. The socket will remain this size until the user begins to prepare for weight bearing, where the pin displacing from proximal to distal and there is a decrease in anterior distal sensed distance. A calibration procedure may be executed on each participant to characterize threshold pin distances for the controller so that the controller properly detects transition from sitting to standing.

The pin sensor may not register the expected changes if the participant does not bear sufficient weight on the distal limb during standing. However, this behavior is highly unlikely for patellar-tendon-bearing and total-surface-bearing socket designs.

Example devices, methods, and systems are described herein. It should be understood the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood aspects of the present disclosure, as generally described herein, and illustrated in the figures, can be arranged, substituted, combined, separated, and designed in a wide variety of different configurations, all of which are explicitly contemplated herein.

Furthermore, the particular arrangements shown in the Figures should not be viewed as limiting. It should be understood other embodiments may include more or less of each element shown in a given Figure. Further, some of the illustrated elements may be combined or omitted. Yet further, an example embodiment may include elements not illustrated in the Figures.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

Specific elements of any foregoing embodiments can be combined or substituted for elements in other embodiments. Moreover, the inclusion of specific elements in at least some of these embodiments may be optional, wherein further embodiments may include one or more embodiments that specifically exclude one or more of these specific elements. Furthermore, while advantages associated with certain embodiments of the disclosure have been described in the context of these embodiments, other embodiments may also exhibit such advantages, and not all embodiments necessarily exhibit such advantages to fall within the scope of the disclosure.

The invention claimed is:

1. An apparatus for automatically adjusting a socket size of a prosthesis, the apparatus comprising:
   the prosthesis having a socket configured to receive a liner arranged over a limb;
   a first opening in a wall of the socket;
   a first panel aligned with the first opening, wherein the first panel includes a first side and a second side opposite the first side;
   a first actuator coupled to the first panel and to the prosthesis, wherein the first actuator includes (i) a frame coupled to the prosthesis via a plurality of supports, wherein the frame is coupled to an electric motor, (ii) a lead screw coupled at a first end to the electric motor and rotatably coupled at a second end to the frame, (iii) at least one travel nut coupled to the lead screw, and (iv) a plurality of linkages coupled to the at least one travel nut and to the first panel, wherein the plurality of linkages translate linear movement of the at least one travel nut along the lead screw into radial movement to advance and retract the first panel, wherein the first actuator is coupled to the first panel between the first side and the second side such that no components of the apparatus contact either the first side of the panel or the second side of the panel, and wherein the first actuator is configured to advance and retract the first panel through the first opening;
   a first sensor coupled to the wall of the socket, wherein the first sensor comprises an inductive sensor, and wherein the first sensor is configured to obtain limb-to-socket gap data corresponding to a distance between a magnetic target positioned in a liner positioned over at least a portion of the limb and the first sensor;
   a second sensor coupled to the socket wall and configured to obtain the limb-to-socket gap data, wherein the second sensor is an inductive sensor, and wherein the second sensor is arranged at an anterior mid-limb location, a posterior-lateral mid-limb location, an anterior-distal location, a posterior-distal location, or an anterior-proximal location; and
   a processor communicatively coupled to the first actuator and to the first sensor and the second sensor, wherein the processor is configured (i) to receive the limb-to-socket gap data, (ii) to determine a socket-size adjustment based on the limb-to-socket gap data and a predetermined socket-fit value, (iii) to generate a command with the socket-size adjustment, and (iv) to send the command with the socket-size adjustment to the first actuator to advance or retract the first panel through the first opening.

2. The apparatus of claim 1, wherein the first sensor is an inductive sensor.

3. The apparatus of claim 1, wherein the first sensor is arranged at a posterior-medial mid-limb location or a posterior-lateral mid-limb location.

4. The apparatus of claim 1, wherein the plurality of linkages comprises a pair of first linkages and a pair of second linkages, the pair of first linkages is rotatably coupled at first ends to opposing sides of the at least one travel nut and rotatably coupled at second ends to opposing sides of a panel mount, wherein the panel mount is coupled to the first panel, and wherein the pair of second linkages is rotatably coupled at first ends to the pair of first linkages and rotatably coupled at second ends to opposing sides of the frame.

5. The apparatus of claim 1, the first actuator further comprises:

a sleeve disposed on the lead screw, wherein the at least one travel nut comprises a first travel nut and a second travel nut arranged on opposing sides of the sleeve, the first travel nut and the second travel nut are arranged such that rotation of the lead screw in a first direction causes the first travel nut and the second travel nut to move toward each other and the sleeve and rotation in a second direction cause the first travel nut and the second travel nut to move away from each other and the sleeve, and wherein the plurality of linkages comprises a pair of first linkages and a pair of second linkages, wherein the pair of first linkages are each rotatably coupled at a first end to the first panel and one of the pair of first linkages is rotatably coupled at a second end to the first travel nut and the other of the pair of first linkages is rotatably coupled at a second end to the second travel nut, and wherein the pair of second linkages are each rotatably coupled at a first end to the sleeve and one of the pair of second linkages is rotatably coupled at a second end to one of the pair of the first linkages and the other of the pair of second linkages is rotatably coupled at a second end to the other of the pair of first linkages.

6. The apparatus of claim 1, wherein the first opening and the first panel are arranged at a posterior location on the wall of the socket.

7. The apparatus of claim 1, further comprising:
a second opening in the wall of the socket;
a second panel aligned with the second opening, wherein the second opening and the second panel are arranged at an anterior-lateral location on the wall of the socket;
a second actuator coupled to the second panel and to the prosthesis, wherein the second actuator is configured to advance and retract the second panel through the second opening;
a third opening in the wall of the socket;
a third panel aligned with the third opening, wherein the third opening and the third panel are arranged at an anterior-medial location on the wall of the socket; and
a third actuator coupled to the third panel and to the prosthesis, wherein the third actuator is configured to advance and retract the third panel through the third opening.

8. The apparatus of claim 1, further comprising:
a pin sensor arranged at a bottom of the socket and configured to receive a locking pin coupled to a liner arranged over the limb, wherein the pin sensor is configured to obtain limb-depth data corresponding to a depth of the limb in the socket, wherein the processor is communicatively coupled to the pin sensor, wherein the processor is further configured (v) to receive the limb-depth data and (vi) to determine the socket-size adjustment further based on the limb-depth data.

9. The apparatus of claim 8, wherein the processor is further configured (vii) to determine a current operating mode is one of a walking mode, a high activity mode, a low activity mode and a rest mode based on the limb-to-socket gap data and the limb-depth data and (viii) to determine the socket-size adjustment further based on the current operating mode.

10. A method for automatically adjusting a socket size of a prosthesis using the apparatus of claim 1, comprising:
receiving, via the processor, the limb-to-socket gap data from the first sensor;
determining, via the processor, a socket-size adjustment based on the limb-to-socket gap data from the first sensor and the predetermined socket-fit value;
generating, via the processor, the command with the socket-size adjustment; and
sending, via the processor, the command with the socket-size adjustment to the first actuator to advance or retract the first panel through the first opening.

11. The method of claim 10, wherein the processor is communicatively coupled to the second sensor, the method further comprising:
receiving, via the processor, limb-to-socket gap data from the second sensor; and
determining, via the processor, the socket-size adjustment further based on the limb-to-socket gap data from the second sensor.

12. The method of claim 10, wherein the apparatus further comprises a pin sensor arranged at a bottom of the socket and configured to receive a locking pin coupled to the limb, wherein the pin sensor is configured to obtain limb-depth data corresponding to a depth of the limb in the socket, wherein the processor is communicatively coupled to the pin sensor, wherein the method further comprises:
receiving, via the processor, the limb-depth data from the pin sensor; and
determining, via the processor, the socket-size adjustment further based on the limb-depth data.

13. The method of claim 12, further comprising:
determining, via the processor, that a current operating mode is one of a walking mode, a high activity mode, a low activity mode and a rest mode based on the limb-to-socket gap data and the limb-depth data; and
determining the socket-size adjustment further based on the current operating mode.

14. The method of claim 13, wherein determining that the current operating mode is the walking mode comprises:
identifying, via the processor, five most recent peak-to-peak amplitudes for five most recent local minima and five most recent local maxima for the distance between the limb and the wall of the socket based on the limb-to-socket gap data;
determining, via the processor, that none of the five most recent peak-to-peak amplitudes is more than 25% greater than an average value of the five most recent peak-to-peak amplitudes and that none of the five most recent peak-to-peak amplitudes is more than 25% less than the average value of the five most recent peak-to-peak amplitudes; and
determining, via the processor, that a cadence time between each successive local minima of the at least five most recent local minima is less than a cadence threshold based on the limb-to-socket gap data.

15. The method of claim 13, wherein the processor is communicatively coupled to the pin sensor, wherein determining that the current operating mode is the low activity mode comprises:
determining, via the processor, a most recent pin height minimum is below a pin height threshold based on the limb-depth data, wherein the pin height threshold is determined by the processor based on pin height minima detected by the pin sensor over a preceding predetermined period of time.

16. The method of claim 13, further comprising:
in response to a determination that the current operating mode is the rest mode, determining, via the processor, that the socket-size adjustment is 1% of the predetermined socket-fit value.

17. The method of claim 10, further comprising:
receiving, via the processor, the predetermined socket-fit value from a user.

18. A non-transitory computer-readable medium having stored thereon program instructions that upon execution by a processor, cause performance of a set of acts using the apparatus of claim 1, the set of acts comprising:

receiving the limb-to-socket gap data from the first sensor;

determining a socket-size adjustment based on the limb-to-socket gap data from the first sensor and the predetermined socket-fit value;

generating the command with the socket-size adjustment; and sending the command with the socket-size adjustment to the first actuator to advance or retract the first panel through the first opening.

* * * * *